(12) United States Patent
Kitamura et al.

(10) Patent No.: US 8,591,414 B2
(45) Date of Patent: Nov. 26, 2013

(54) SKIN STATE ANALYZING METHOD, SKIN STATE ANALYZING APPARATUS, AND COMPUTER-READABLE MEDIUM STORING SKIN STATE ANALYZING PROGRAM

(75) Inventors: Naomi Kitamura, Yokohama (JP); Yuji Masuda, Yokohama (JP); Hiroyuki Ohnishi, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/405,807

(22) Filed: Feb. 27, 2012

(65) Prior Publication Data

US 2012/0157821 A1 Jun. 21, 2012

Related U.S. Application Data

(62) Division of application No. 11/912,916, filed as application No. PCT/JP2006/308464 on Apr. 21, 2006, now abandoned.

(30) Foreign Application Priority Data

Apr. 28, 2005 (JP) ................... 2005-133275
Nov. 8, 2005 (JP) ................... 2005-324117

(51) Int. Cl.
*A61B 5/00* (2006.01)
*G06K 9/00* (2006.01)

(52) U.S. Cl.
USPC .......................................... 600/306; 382/128

(58) Field of Classification Search
USPC .......... 600/306, 346–347; 382/115, 118, 162, 382/165, 128; 348/77
See application file for complete search history.

(56) References Cited

U.S. PATENT DOCUMENTS

| | | | |
|---|---|---|---|
| 6,571,003 B1* | 5/2003 | Hillebrand et al. | 382/118 |
| 6,587,711 B1 | 7/2003 | Alfano et al. | |
| 7,336,810 B2 | 2/2008 | Fujii et al. | |
| 2004/0214336 A1 | 10/2004 | Hirai et al. | |
| 2004/0215066 A1 | 10/2004 | Huang et al. | |
| 2004/0218810 A1* | 11/2004 | Momma | 382/162 |

(Continued)

FOREIGN PATENT DOCUMENTS

| | | |
|---|---|---|
| EP | 0 516 457 A2 | 12/1992 |
| JP | 07-323013 A | 12/1995 |

(Continued)

OTHER PUBLICATIONS

USPTO RR mailed Dec. 27, 2011 in connection with U.S. Appl. No. 11/912,916.

(Continued)

*Primary Examiner* — Navin Natnithithadha
*Assistant Examiner* — Eric Messersmith
(74) *Attorney, Agent, or Firm* — Ladas & Parry LLP

(57) ABSTRACT

A skin state analyzing method for analyzing the skin state of an examinee using an image of the skin of the examinee includes an analyzing step of analyzing at least one of texture/pores, spots, skin tone, and sebum of the skin from the image, a storing step of storing the image and an analysis result obtained from the analyzing step in association with skin examination date/time information and examinee information, a display screen generating step of generating a screen displaying the image and the analysis result of the examinee stored in the storing step, and an output step of outputting the information generated in the display screen generating step.

21 Claims, 24 Drawing Sheets

(56) References Cited

U.S. PATENT DOCUMENTS

| | | | |
|---|---|---|---|
| 2006/0092315 A1* | 5/2006 | Payonk et al. | 348/370 |
| 2007/0092160 A1 | 4/2007 | Fujii et al. | |
| 2009/0136101 A1* | 5/2009 | Chhibber et al. | 382/128 |

FOREIGN PATENT DOCUMENTS

| | | |
|---|---|---|
| JP | 09-154832 A | 6/1997 |
| JP | 2001-000419 A | 1/2001 |
| JP | 2003-024283 A | 1/2003 |
| JP | 2003-070749 A | 3/2003 |
| JP | 2003-190104 A | 7/2003 |
| JP | 2003-199727 A | 7/2003 |
| JP | 2003-345895 A | 12/2003 |
| JP | 2004-105748 A | 4/2004 |
| JP | 2004-121858 A | 4/2004 |
| JP | 2004-201797 A | 7/2004 |
| JP | 2004-215991 A | 8/2004 |
| JP | 2004-230117 A | 8/2004 |
| JP | 2005-034355 A | 2/2005 |
| JP | 2005-034424 A | 2/2005 |
| JP | 2005-080774 A | 3/2005 |
| JP | 2005-190104 A | 7/2005 |
| JP | 2005-221266 A | 8/2005 |
| TW | 200428231 A | 12/2004 |
| WO | 2004/093844 A1 | 11/2004 |

OTHER PUBLICATIONS

International Search Report: mailed May 16, 2006; PCT/JP2006/308464.

Taiwanese Office Action mailed Jan. 19, 2012 in connection with Taiwanese patent application 95114939.

European Search Report dated Aug. 6, 2012; Appln. No. EP 12 00 0921.2.

Supplementary European Search Report mailed May 30, 2012; Appln No./Patent No. 06732222.2-1526 / 1875863 PCT/JP2006308464.

* cited by examiner

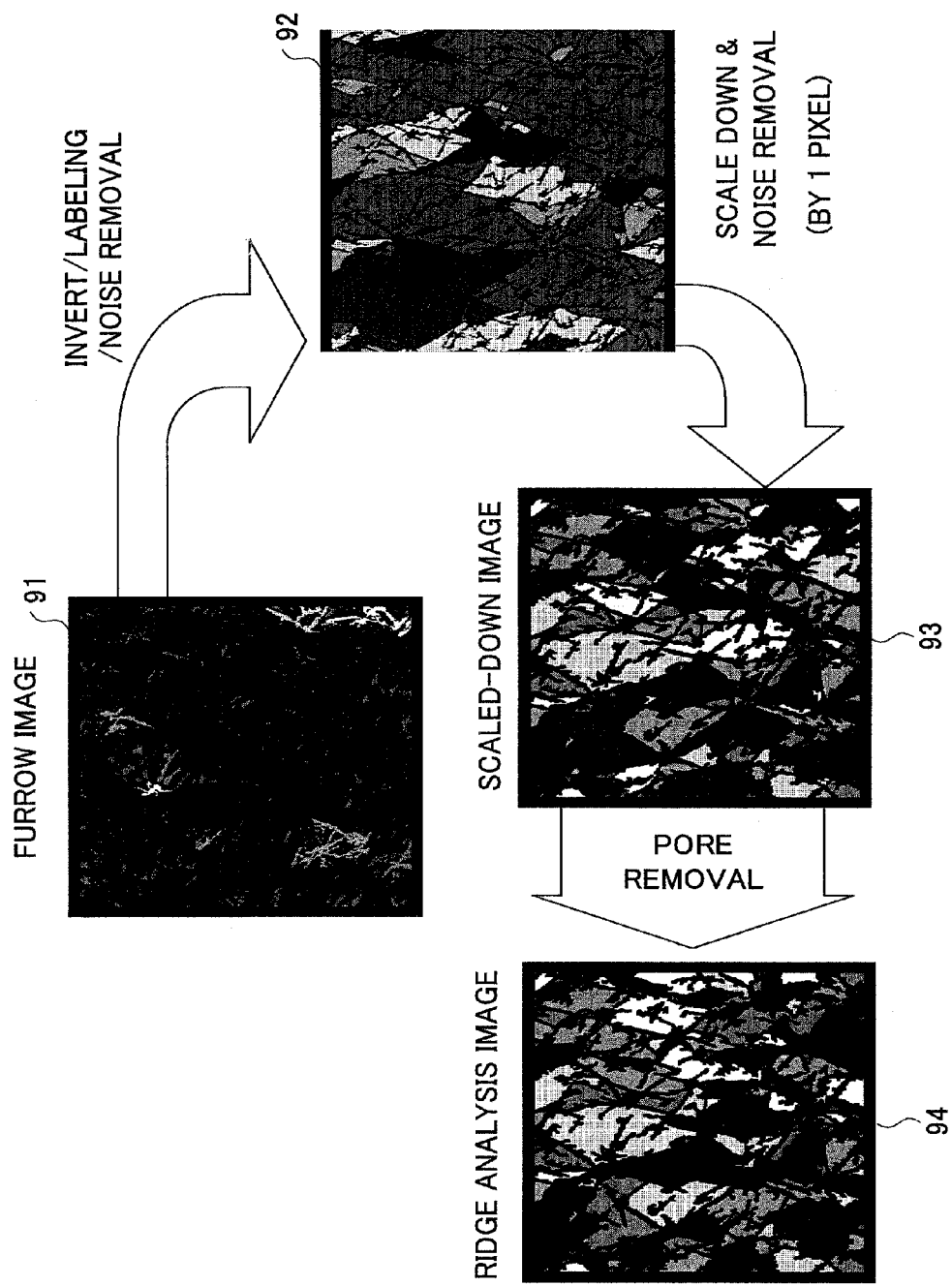

FIG.16

MEMBER INFORMATION
FILE No. A0001
NAME TSUBAKI HANAKO
DATE OF BIRTH 1980/07/07
GENDER FEMALE
EXAMINED AREA

EXAMINATION LOG

| LOG No. | EXAMINATION DATE | TEXTURE /PORE | SPOTS | SKINTONE | SEBUM |
|---|---|---|---|---|---|
| 12 | 2005/08/20 | ● | | | ● |
| 11 | 2005/08/19 | | ● | ● | ● |
| 10 | 2005/08/18 | ● | ● | | ● |
| 09 | 2005/08/17 | ● | | ● | ● |
| 08 | 2005/08/16 | ● | ● | ● | |
| 07 | 2005/08/15 | | ● | ● | ● |
| 06 | 2005/08/14 | ● | ● | | ● |
| 05 | 2005/08/13 | | ● | ● | ● |
| 04 | 2005/08/12 | ● | ● | ● | ● |
| 03 | 2005/08/11 | ● | ● | | |
| 02 | 2005/08/10 | | | ● | ● |
| 01 | 2005/08/09 | ● | ● | | ● |

SKIN STATE ANALYZING METHOD, SKIN STATE ANALYZING APPARATUS, AND COMPUTER-READABLE MEDIUM STORING SKIN STATE ANALYZING PROGRAM

TECHNICAL FIELD

The present invention relates generally to a skin state analyzing method, a skin state analyzing apparatus, and a computer-readable medium storing a skin state analyzing program and particularly to a skin state analyzing method, a skin state analyzing apparatus, and a computer-readable medium storing a skin state analyzing program for accurately performing multidimensional skin state analysis.

BACKGROUND ART

Various techniques have been proposed in the prior art related to analyzing the skin state in the field of cosmetic counseling and medicine. For example, Patent Documents 1 and 2 disclose techniques that involve imaging the surface of certain areas of the skin having wrinkles, pores, spots, and freckles, for example, with a microscope to analyze the obtained image.
Patent Document 1: Japanese Laid-Open Patent Publication No. 2003-24283
Patent Document 2: Japanese Laid-Open Patent Publication No. 7-323013

However, the prior art does not disclose an analyzing apparatus that uses skin information of an examinee that is obtained by a measuring device including a microscope as is described above to analyze the texture, pores, spots, skin tone, and the amount of sebum in the skin for accurately evaluating the skin, and representing the analysis results as numerical values. Also, techniques are not disclosed for displaying the analysis results in an easily discernible manner to the examinee, a counselor, or a doctor, for example, to enable multidimensional analysis and evaluation.

DISCLOSURE OF THE INVENTION

Aspects of the present invention are directed to solving one or more of the above-described problems of the related art and providing a skin state analyzing method, a skin state analyzing apparatus, and a computer-readable medium storing a skin state analyzing program for accurately performing multidimensional skin state analysis.

According to one embodiment of the present invention, a skin state analyzing method is provided that includes an analyzing step of analyzing at least one of texture/pores, spots, skin tone, and sebum of the skin from the image; a storing step of storing the image and an analysis result obtained from the analyzing step in association with skin examination date/time information and examinee information; a display screen generating step of generating a screen displaying the image and the analysis result of the examinee stored in the storing step; and an output step of outputting the information generated in the display screen generating step. In this way, multidimensional analysis of the skin state may be accurately performed based on the skin texture/pores, spots, skin tone, and/or sebum analysis results.

In one preferred embodiment, the display screen generating step may involve displaying the analysis result of the examinee in association with an evaluation relative to age distribution that is stored beforehand. In this way, the analysis result of the examinee may be compared with data of persons of the same age group (same generation) of the examinee to enable multidimensional analysis according to the examinee.

In a further preferred embodiment, the display screen generating step may involve defining at least one evaluation range for classifying the skin state within the age distribution and displaying the defined evaluation range in association with the analysis result. In this way, the accurate analysis of the skin state may be enabled.

In another preferred embodiment, the display screen generating step may involve displaying a progressive skin state analysis by displaying a plurality of analysis results including a latest analysis result of the examinee and one or more past analysis results of the examinee stored in the storing step. In this way, progressive state change may be accurately determined. Thus, multidimensional analysis according to the examinee may be enabled.

In another preferred embodiment, the display screen generating step may involve displaying time intervals of a time axis in proportion to time length or a number of analysis results displayed. In this way various time displays may be enabled. Also, since time display in proportion to actual time lapse may realized, the skin state on dates other than the examination date may be easily estimated.

According to another embodiment of the present invention, a skin state analyzing method is provided for analyzing skin texture or pores of an examinee using an image of the skin of the examinee, the method including a parameter generating step of generating at least one parameter pertaining to at least one of a pore size, furrow width, ridge fineness, and ridge shape obtained from the image; and a parameter analyzing step of analyzing the skin texture or pores based on the parameter generated in the parameter generating step. In this way, the skin texture/pores of the examinee may be accurately analyzed.

In one preferred embodiment, the parameter generating step may involve using a pore area obtained from the image in generating the parameter pertaining to the pore size, using a furrow width obtained from the image in generating the parameter pertaining to the furrow width, using a number of ridges or an average area of ridges obtained from the image in generating the parameter pertaining to the ridge fineness, and using a roundness of ridges obtained from the image in generating the parameter pertaining to the ridge shape. In this way, information on the skin texture/pores obtained from the skin image may be easily and accurately analyzed using parameters that may be represented by numerical values, for example.

According to another embodiment of the present invention, a skin state analyzing method is provided for analyzing skin texture or pores of an examinee using an image of the skin of the examinee, the method including an RGB component extracting step of extracting R components, G components, and B components from the image; a pore image extracting step of extracting a pore image from the R components and the B components or G components obtained in the RGB component extracting step; a pore parameter generating step of generating a parameter pertaining to pore size from the pore image; a furrow image extracting step of extracting a furrow image from the G components obtained in the RGB component extracting step; a furrow parameter generating step of generating a parameter pertaining to furrow width from the furrow image; a ridge image extracting step of extracting a ridge image from the pore image and the furrow image; a ridge parameter generating step of generating a parameter pertaining to ridge fineness and/or ridge shape from the ridge image; and a parameter analyzing step of analyzing the skin texture or pores using at least one of the parameters generated in the pore parameter generating step, the furrow parameter generating step, and the ridge parameter generating step. In this way, the skin texture/pores of the examinee may be accurately analyzed.

In one preferred embodiment, the pore image extracting step may involve generating a difference image from the R components and the B components or G components and removing furrows from the generated difference image to extract the pore image. By using the difference image generated from the R components and the B components or G components, the pore image may be accurately extracted.

In another preferred embodiment, the pore parameter generating step may involve calculating an average area and/or a total area of pores of the pore image and generating the pore parameter based on the calculated area. In this way, a parameter based on the pores that is represented by a numerical value may be accurately obtained. Also, consistent analysis may be performed even by non-experts based on the parameters.

In another preferred embodiment, the furrow image extracting step may involve performing a filtering process on an image of the G components using a differential filter for emphasizing the furrow shape to extract the furrow image. By performing a filtering process by a differential filter for emphasizing the furrow shape using the G components, pore removal and furrow emphasis may be accurately performed. Accordingly, the furrow image may be accurately extracted.

In another preferred embodiment, the furrow parameter generating step may involve generating the furrow parameter based on a furrow width obtained from the furrow image. In this way, a parameter based on the furrows that is represented by a numerical value may be accurately obtained. Also, consistent analysis may be performed even by non-experts based on the parameters.

In another preferred embodiment, the ridge image extracting step may involve obtaining ridge portions from the furrow image, scaling down peripheries of the ridge portions by a predetermined number of pixels to generate a ridge separated image, and removing pores from the ridge separated image based on the pore image to extract the ridge image.

In this way, plural ridges that are connected to each other may be prevented from being regarded as one ridge and erroneous analysis may be avoided so that the average area or the number of ridges may be accurately obtained.

In another preferred embodiment, the ridge parameter generating step may involve generating the ridge parameter based on an average area or a number of ridges within a predetermined image region of the ridge image, an average area or a number of ridges with respect to a face surface area of the examinee, and/or a ridge roundness. In this way, parameters represented by numerical values based on the average area or the number of ridges within a predetermined image region of the ridge image, the average area or the number of ridges with respect to a face surface area of the examinee, and/or the ridge roundness may be accurately obtained. Also, consistent analysis may be performed even by non-experts based on the parameters.

In another preferred embodiment, the parameter analyzing step may involve displaying at least one of the pore parameter, the furrow parameter, the ridge parameter, the pore image, the furrow image, and the ridge image in a distinguishing color, and displaying adjacent pores, furrows, and ridges using different colors. In this way, individual pore portions, furrow portions, and/or ridge portions may be clearly displayed in a visibly distinguishable manner. Thus, a user may easily determine the shapes, sizes, and numbers of pores and ridges, for example.

According to further embodiments of the present invention, skin state analyzing apparatuses as described below are provided.

According to one embodiment of the present invention, a skin state analyzing apparatus is provided that analyzes a skin state of an examinee using an image of the skin of the examinee, the apparatus including analyzing means for analyzing at least one of skin texture/pores, spots, skin tone, and sebum from the image; storage means for storing the image and an analysis result obtained by the analyzing means in association with a date/time of examination of the skin of the examinee and examinee information; display screen generating means for generating a screen displaying the image and the analysis result of the examinee stored by the storage means; and output means for outputting information generated by the display screen generating means. In this way, multidimensional skin state analysis may be accurately performed based on the skin texture/pores, spots, skin tone, and/or sebum analysis results.

In a preferred embodiment, the display screen generating means may display the analysis result of the examinee in association with an evaluation relative to age distribution that is stored beforehand. In this way, the analysis result of the examinee may be compared with data of persons of the same age group (same generation) as the examinee so that multidimensional analysis according to the examinee may be possible.

In a further preferred embodiment, the display screen generating means may define at least one evaluation range for classifying the skin state within the age distribution and display the defined evaluation range in association with the analysis result. In this way, accurate skin state analysis may be enabled.

In another preferred embodiment, the display screen generating means may display a progressive skin state analysis by displaying a plurality of analysis results including a latest analysis result of the examinee and one or more past analysis results of the examinee stored by the storage means. In this way, progressive state change may be accurately determined. Thus, multidimensional analysis according to the examinee may be enabled.

According to another preferred embodiment, the display screen generating means may display time intervals of a time axis in proportion to time length or a number of analysis results displayed. In this way, various time displays may be realized. Also, since time display in proportion to actual time lapse may realized, the skin state on dates other than the examination date may be easily estimated.

According to another embodiment of the present invention, a skin state analyzing apparatus is provided for analyzing skin texture or pores of an examinee using an image of the skin of the examinee, the apparatus including RGB component extracting means for extracting R components, G components, and B components from the image; pore image extracting means for extracting a pore image from the R components and the B components or G components obtained by the RGB component extracting means; pore parameter generating means for generating a parameter pertaining to pore size from the pore image; furrow image extracting means for extracting a furrow image from the G components obtained by the RGB component extracting means; furrow parameter generating means for generating a parameter pertaining to furrow width from the furrow image; ridge image extracting means for extracting a ridge image from the pore image and the furrow image; ridge parameter generating means for generating a parameter pertaining to ridge fineness and/or ridge shape from the ridge image; and parameter analyzing means for analyzing the skin texture or pores using at least one of the parameters generated by the pore parameter generating means, the furrow parameter generating means, and the ridge parameter generating means. In this way, the skin texture/pores of the examinee may be accurately analyzed.

In one preferred embodiment, the pore image extracting means may generate a difference image from the R components and the B components or G components and remove furrows from the generated difference image to extract the pore image. By using the difference image generated from the R components and the B components or G components, the pore image may be accurately extracted.

In another preferred embodiment of the present invention, the pore parameter generating means may calculate an average area and/or a total area of pores of the pore image and generate the pore parameter based on the calculated area. In this way, a parameter based on the pores that is represented by a numerical value may be accurately obtained. Also, consistent analysis may be performed even by non-experts based on the parameters.

In another preferred embodiment, the furrow image extracting means may perform a filtering process on an image of the G components using a differential filter for emphasizing the furrow shape to extract the furrow image. By performing a filtering process by a differential filter for emphasizing the furrow shape using the G components, pore removal and furrow emphasis may be accurately performed. Accordingly, the furrow image may be accurately extracted.

In another preferred embodiment, the furrow parameter generating means may generate the furrow parameter based on a furrow width obtained from the furrow image. In this way, a parameter based on the furrows that is represented by a numerical value may be accurately obtained. Also, consistent analysis may be performed even by non-experts based on the parameters.

In another preferred embodiment, the ridge image extracting means may obtain ridge portions from the furrow image, scale down peripheries of the ridge portions by a predetermined number of pixels to generate a ridge separated image, and remove pores from the ridge separated image based on the pore image to extract the ridge image. In this way, plural ridges that are connected to each other may be prevented from being regarded as one ridge and erroneous analysis may be avoided so that the average area or the number of ridges may be accurately obtained.

In another preferred embodiment, the ridge parameter generating means may generate the ridge parameter based on an average area or a number of ridges within a predetermined image region of the ridge image, an average area or a number of ridges with respect to a face surface area of the examinee, and/or a ridge roundness. In this way, parameters represented by numerical values based on the average area or the number of ridges within a predetermined image region of the ridge image, the average area or the number of ridges with respect to a face surface area of the examinee, and/or the ridge roundness may be accurately obtained. Also, consistent analysis may be performed even by non-experts based on the parameters.

In another preferred embodiment, the parameter analyzing means may display at least one of the pore parameter, the furrow parameter, the ridge parameter, the pore image, the furrow image, and the ridge image in a distinguishing color, and displays adjacent pores, furrows, and ridges using different colors. In this way, individual pore portions, furrow portions, and/or ridge portions may be clearly displayed in a visibly distinguishable manner. Thus, a user may easily determine the shapes, sizes, and numbers of pores and ridges, for example.

Further embodiments of the present invention relate to a computer-readable medium storing a skin state analyzing program as is described below.

According to one embodiment of the present invention, a computer-readable medium storing a skin state analyzing program is provided, which program, when executed by a computer, causes the computer to perform a skin state analyzing process for analyzing a skin state of an examinee using an image of the skin of the examinee, the skin state analyzing process including an analyzing process for analyzing at least one of skin texture/pores, spots, skin tone, and sebum from the image; a storage process for storing the image and an analysis result obtained by the analyzing process in association with a date/time of examination of the skin of the examinee and examinee information; a display screen generating process for generating a screen displaying the image and the analysis result of the examinee stored by the storage process; and an output process for outputting information generated by the display screen generating process.

According to another embodiment of the present invention, a computer-readable medium storing a skin state analyzing program is provided which program, when executed by a computer, causes the computer to perform a skin state analyzing process for analyzing skin texture or pores of an examinee using an image of the skin of the examinee, the skin state analyzing process including an RGB component extracting process for extracting R components, G components, and B components from the image; a pore image extracting process for extracting a pore image from the R components and the B components or G components obtained by the RGB component extracting process; a pore parameter generating process for generating a parameter pertaining to pore size from the pore image; a furrow image extracting process for extracting a furrow image from the G components obtained by the RGB component extracting process; a furrow parameter generating process for generating a parameter pertaining to furrow width from the furrow image; a ridge image extracting process for extracting a ridge image from the pore image and the furrow image; a ridge parameter generating process for generating a parameter pertaining to ridge fineness and/or ridge shape from the ridge image; and a parameter analyzing process for analyzing the skin texture or pores using at least one of the parameters generated by the pore parameter generating process, the furrow parameter generating process, and the ridge parameter generating process.

According to embodiments of the present invention, multidimensional skin state analysis may be accurately performed.

BRIEF DESCRIPTION OF THE DRAWINGS

FIG. 13 is a diagram showing exemplary images that may be obtained during the ridge image extraction process;

FIG. 16 is a diagram showing an exemplary examination log display screen;

BEST MODE FOR CARRYING OUT THE INVENTION

In the following, preferred embodiments of the present invention are described with reference to the accompanying drawings.

<System Configuration>

Figure 1:
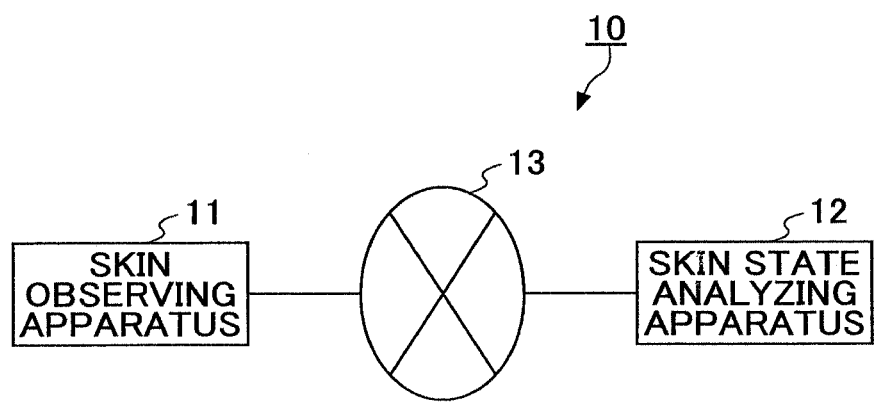
FIG. 1 is a diagram showing an exemplary configuration of a skin state analyzing system according to an embodiment of the present invention.

FIG. 1 is a diagram showing an overall configuration of a skin state analyzing system according to an embodiment of the present invention. The illustrated skin state analyzing system 10 of FIG. 1 includes a skin observing apparatus 11 and a skin state analyzing apparatus 12. The skin observing apparatus 11 and the skin state analyzing apparatus 12 are interconnected by a communications network 13 such as the Internet or a LAN (local area network) to enable data transmission/reception.

The skin observing apparatus 11 may capture a skin image of an examinee using a CCD (Charge Coupled Device) camera to obtain an image of a certain skin area of the examinee or a magnified image of this skin area magnified by a predetermined power, for example. According to certain preferred embodiments of the present invention, a SMA (Skin Micro Analyzer) skin magnifying microscope system or a skin surface state observing apparatus as disclosed in Patent Document 1 (Japanese Laid-Open Patent Publication No. 2003-24283) may be used for imaging the face or skin. However, the present invention is not limited to such embodiments.

The skin observing apparatus 11 acquires information on at least one of the skin texture/pores, spots, skin tone, or the amount of sebum of the skin. Also, the skin observing apparatus 11 transmits the acquired information such as captured image information to the skin state analyzing apparatus 12 via the communications network 13.

The skin state analyzing apparatus 12 analyzes at least one of the skin texture/pores, spots, skin tone, or the amount of sebum of the skin based on the image transmitted from the skin observing apparatus 11, provides analyses related to age distribution and age-based change in addition to the analysis results and image observations, and displays such information on a display screen.

It is noted that the system configuration shown in FIG. 1 includes one skin observing apparatus 11 and one skin state analyzing apparatus 12; however, the present invention is not limited to such a configuration and the skin state analyzing system may include plural skin observing apparatuses 11 and/or skin state analyzing apparatuses 12. In other examples, the component elements of the skin observing apparatus 11 for capturing an image of the skin of an examinee may be arranged within the skin state analyzing apparatus 12, or in the case where image information to be used in skin state analysis is already available, the skin observing apparatus 11 may not have to be provided.

In the skin state analyzing system 10 as is shown in FIG. 1, the processes performed using the skin observing apparatus 11 may correspond to pre-processes to be performed before actual skin diagnosis or analysis. Accordingly, an assistant such as a medical staff member assisting a doctor may perform these processes. On the other hand, processes performed using the skin state analyzing apparatus 12 may correspond to processes to be performed by the person actually conducting the skin diagnosis or analysis such as a doctor.

<Skin Observing Apparatus 11>

Figure 2:
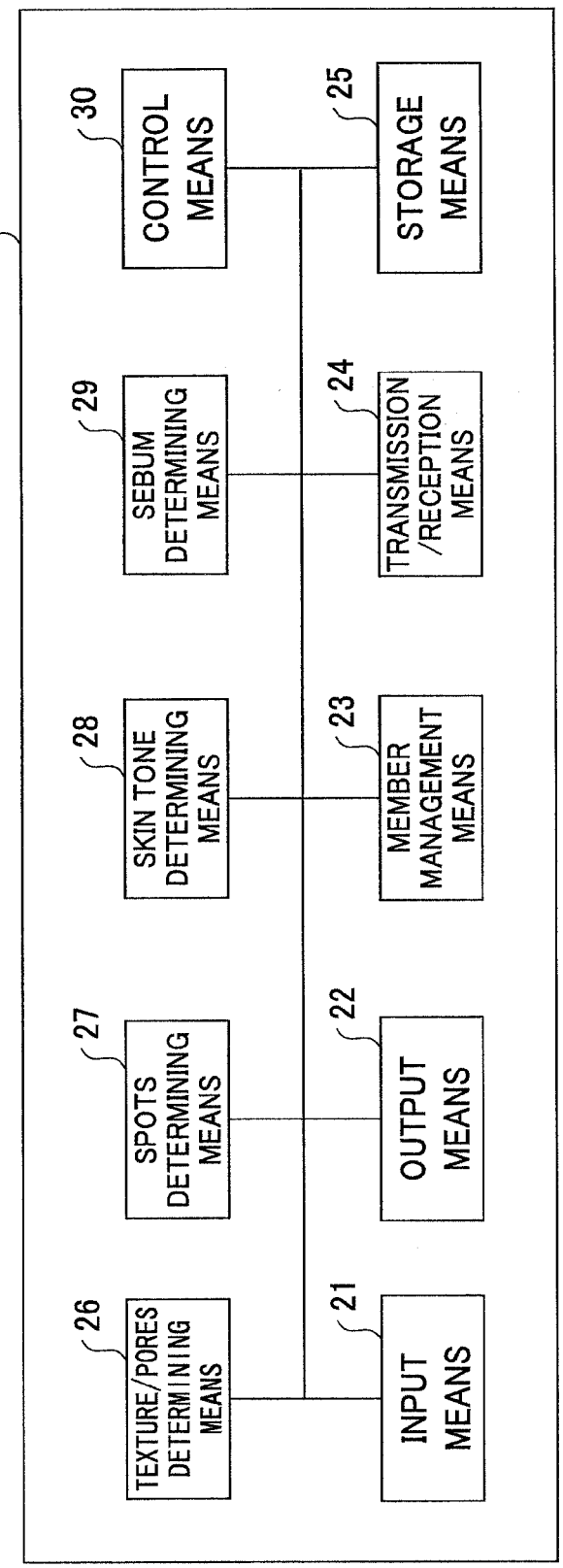
FIG. 2 is a diagram showing an exemplary functional configuration of a skin observing apparatus.

In the following, a functional configuration of the skin observing apparatus 11 is described. FIG. 2 is a diagram showing an exemplary functional configuration of the skin observing apparatus 11. The skin observing apparatus 11 as is shown in FIG. 2 includes input means 21, output means 22, member management means 23, transmission/reception means 24, storage means 25, texture/pores determining means 26, spots determining means 27, skin tone determining means 28, sebum determining means 29, and control means 30.

The input means 21 accepts inputs of various data from a user upon registering information on members that are subject to counseling (examinee) and the examination time/date, for example. Also, the input means 21 accepts instructions from a user to perform certain determinations or transmit data to the skin state analyzing apparatus 12, for example. In certain preferred embodiments, the input means 21 may be a keyboard or a pointing device such as a mouse.

The output means 22 displays/outputs information input by the input means 21 and processed information obtained based on the input information, for example. In certain preferred embodiments, the output means 22 may be a display or a speaker. In another embodiment, the output means 22 may include a printer function for printing out determination results on a printing medium and providing the printed output to the user or the examinee, for example.

The member management means 23 manages information including personal information of members and the number of examinations conducted, for example. Specifically, the member management means 23 may register information on members, or call/reference/correct/delete member information or determination information already stored in the storage means 25, for example.

In one example, information on items such as "file number", "name", "date of birth", "gender", "examination area", and "memo (remarks)" may be registered as member information for identifying each member and/or examination result. However, member information to be registered is not limited to such an example, and in another example, information on "age group" may be registered instead of the information item "date of birth". Also, in certain preferred embodiments, the above-mentioned information item "file number" or "name" may be used to call information pertaining to a certain member.

The transmission/reception means 24 is a communications interface for enabling data transmission/reception between the skin observing apparatus 11 and the skin state analyzing apparatus 12 via the communications network 13. Accordingly, when the skin observing apparatus 11 receives via the transmission/reception means 24 an acquisition request from the skin state analyzing apparatus 12 requesting for information such as member information and/or determination information, or when the skin observing apparatus 11 accepts transmission instructions via the input means 21 to transmit information to the skin state analyzing apparatus 12, the skin observing apparatus 11 uses the transmission/reception means 24 to transmit relevant information to the skin state analyzing apparatus 12 via the communications network 13.

The storage means 25 stores various types of information such as member information and determination information acquired from the member management means 23. Also, the storage means 25 stores determination results obtained from the texture/pores determining means 26, the spots determining means 27, the skin tone determining means 28, and the sebum determining means 29 in association with determination time/date information and/or member information, for example.

The texture/pore determining means 26 acquires image data of skin texture and pores by imaging an area of the skin subject to observation using an optical system that actively acquires surface reflection light of light incident to the skin area being observed. Specifically, a microscope may be used in which a deflection filter is arranged in front of an LED (Light Emitting Diode) and a CCD to enable acquisition of specular light (light with the same deflection as the irradiation light) so that roughness of the skin surface may be clearly identified in imaging the skin texture and pores, for example. In this way, surface reflection light may be actively acquired. The image data (determination data) acquired by the texture/pore determining means 26 are stored in the storage means 25.

The spots determining means 27 acquires image data of spots by imaging an area of the skin subject to observation using an optical system that actively acquires internal diffusion light of light incident to the skin area being observed. Specifically, a microscope may be used in which a deflection filter is arranged in front of an LED (Light Emitting Diode) and a CCD to enable acquisition of internal diffusion light (light with a deflection perpendicular to the irradiation light) so that light from the interior may be acquired in imaging spots of the skin, for example. In this way, internal diffusion light may be actively acquired. The image data (determination data) acquired by the spots determining means 27 are stored in the storage means 25.

It is noted that the texture/pores determining means 26 and the spots determining means 27 may each have individual deflection filters, or a mechanism may be arranged at the microscope for switching the deflection filter, for example. In switching the deflection filter, a technique disclosed in Patent Document 2 (Japanese Laid-Open Patent Publication No. 7-323013) may be used, for example.

The skin tone determining means 28 acquires image data of the skin tone by imaging an area of the skin subject to observation using an optical system that acquires all available light that may be acquired from light incident on the skin area being observed. As is described above, in the case of imaging the skin texture or spots, an optical system that actively acquires specular light or internal diffusion light is used. On the other hand, in the case of imaging the skin tone, an optical system that does not employ a filter and acquires all available light, that is, all the light reflected by the skin, may be used. In addition to capturing an image of the skin, the skin tone determining means 28 captures an image of a correction plate used for correcting the color of the captured image of the skin. It is noted that the correction plate is used each time skin tone determination is performed, and the RGB values of the correction plate are determined beforehand. Specifically, using the correction plate, a relational expression between intrinsic RGB values of the correction plate and RGB values obtained by imaging the correction plate and detecting the image light at a CCD is created, and the relational expression is used to correct the RGB color values of the skin tone obtained by detecting image light of the skin tone at the CCD into intrinsic RGB values of the skin tone. It is noted that the skin tone determining means 28 may capture the images of the skin and the correction plate in either order. The image data obtained by the skin tone determining means 28 are stored in the image data storage means 25.

The sebum determining means 29 determines the amount of sebum of the skin by pressing a lipid marker on an area of the skin for a certain period of time and capturing an image of the lipid marker. The lipid marker absorbs sebum on the skin upon coming into contact with the skin and the color of the lipid marker changes at the absorbed portion. Based on the color change of the lipid marker represented by the image captured by the sebum determining means 29 using a microscope, the skin state analyzing apparatus 12 may analyze the captured image to represent the amount of sebum absorbed by a numerical value. The image data acquired by the sebum determining means 29 are stored in the storage means 25.

The control means 30 controls overall operations of the component elements of the skin observing apparatus 11. Specifically, the control means 30 may control determination operations of corresponding determination means based on instructions input by a user via the input means 21 designating the examination time/date and the area to be examined, for example, registration of relevant information in the storage means 25, and transmission of various types of data to the skin state analyzing apparatus 12, for example.

<Skin State Analyzing Apparatus 12>

Figure 3:
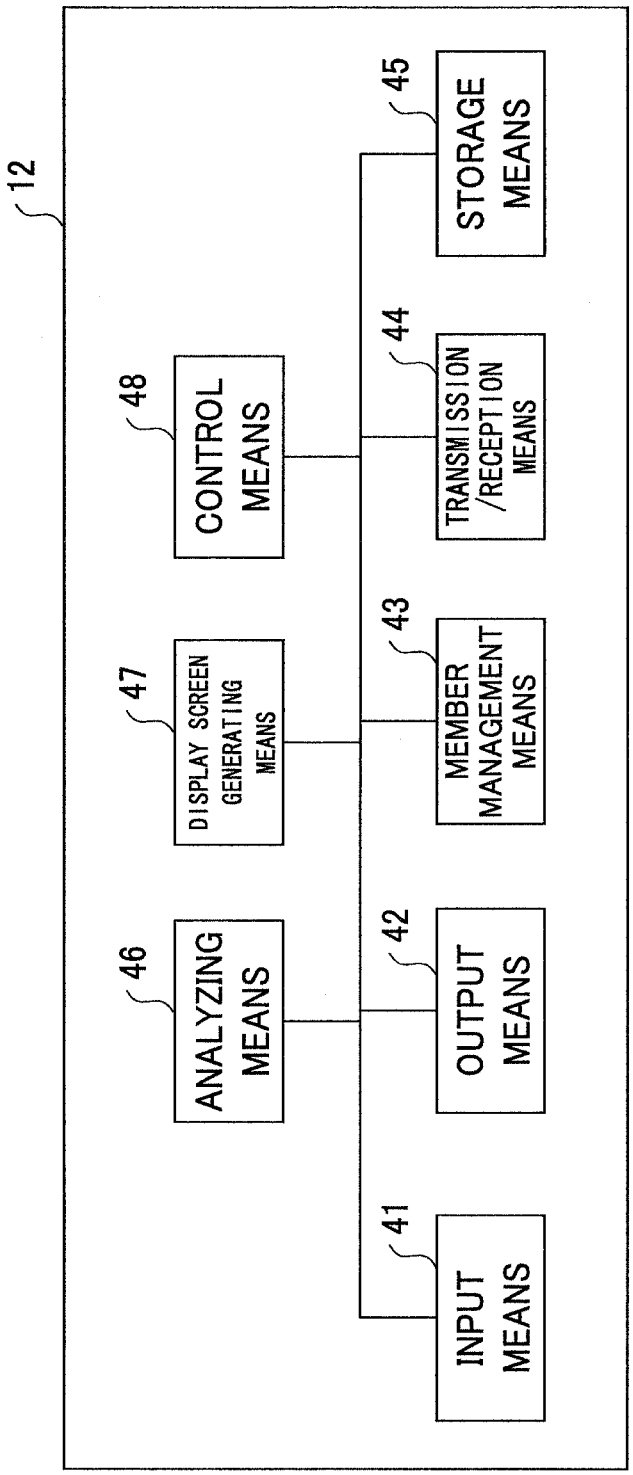
FIG. 3 is a diagram showing an exemplary functional configuration of a skin state analyzing apparatus.

In the following, a functional configuration of the skin state analyzing apparatus 12 is described. FIG. 3 is a diagram showing an exemplary functional configuration of the skin state analyzing apparatus 12. According to FIG. 3, the skin state analyzing apparatus 12 includes input means 41, output means 42, member management means 43, transmission/reception means 44, storage means 45, analyzing means 46, display screen generating means 47, and control means 48.

The input means 41 accepts various data inputs upon instructing the skin state analyzing apparatus 12 to perform various operations such as calling member information obtained from the skin observing apparatus 11 and stored in the storage means 45, analyzing and evaluating various types of data obtained from the skin observing apparatus 11, and displaying the evaluation results, for example. The input means 41 may be a keyboard or a pointing device such as a mouse, for example.

The output means 42 displays data input via the input means 41 and data obtained based on the input data. The output means 41 may be a display or a speaker, for example. Also, the output means 41 may include a printer function, and in such a case, the examination results may be printed out on a printing medium such as paper and provided to the user or the examinee, for example.

The member management means 43 manages information including personal information of members and the number of examinations, for example. Specifically, the member management means 43 may register information on members, or call/reference/correct/delete member information already stored in the storage means 45, for example. It is noted that the member information stored in the storage means 45 may be substantially identical to the information items registered in the skin observing apparatus 11 as is described above.

The transmission/reception means 44 is a communications interface for enabling data transmission/reception between the skin state analyzing apparatus 12 and the skin observing apparatus 11 via the communications network 13. Thus, the skin state analyzing apparatus 12 may receive various types of determination information obtained by the skin observing apparatus 11 at the transmission/reception means 44 via the communications network 13. Also, the skin state analyzing apparatus 12 may transmit requests for various types of information to the skin observing apparatus 11 and acquire information that is not yet transmitted thereto from the skin observing apparatus 11 via the transmission/reception means 44.

The storage means 45 stores various types of information such as member information and determination information acquired from skin observing apparatus 11, analyzing results obtained by the analyzing means 46, diagnoses (evaluations) made by a counselor or a doctor based on the analyzing results displayed by the display screen generating means 47, for example. It is noted that the storage means 45 stores the determination information, analyzing results, and evaluations in association with determination time/date information and member information, for example.

The analyzing means 46 performs at least one analysis one each of the determination results pertaining to skin texture/pores, spots, skin tone, or the amount of sebum obtained at the skin observing apparatus 11. Specifically, with respect to an input of the texture/pores determination result, the analyzing means 46 may generate a numerical value for at least one of the information items "ridge fineness", "ridge shape", "furrow width", or "pore size" representing skin texture characteristics. In generating a numerical value for the information items, R components, G components, and B components are extracted from the captured image of the skin of the examinee, and a pore image is extracted from the extracted R components, B components, and G components. A value representing the pore size may be obtained from the pore image. Also, a furrow (sulcus cutis) image may be extracted from the G components, and a numeric value representing the furrow width may be obtained from the extracted furrow image. Further, a ridge (crista cutis) image may be extracted from the pore image and the furrow image, and values representing the fineness and shape of the ridge may be obtained from the extracted ridge image. It is noted that numerical analysis techniques employed by the analyzing means 46 to analyze the skin texture/pores are described below.

With respect to the spots determination result, the analyzing means 46 does not perform the above-described numerical analysis. That is, the spots determination result is displayed by the display screen generating means 47 so that it may be observed and evaluated by a counselor or a doctor, for example.

With respect to the skin tone determination result, the analyzing means 46 calculates at least one of the hue, brightness (or value), amount of melanin, or amount of hemoglobin from the RGB values of the image corrected by a correction plate.

For example, the hue and the brightness may be calculated using a conventional technique to convert the RGB values into HLS (H: hue, L: luminosity, S: saturation) values to obtain the values of H (hue) and L (luminosity). In the case of obtaining the amount of melanin or the amount of hemoglobin, corresponding values may be calculated based on the formulae disclosed in Patent Document 1 (Japanese Laid-Open Patent Publication No. 2003-24283), for example.

Also, with respect to the sebum determination result, the analyzing means 46 obtains a numerical value representing the area of the lipid marker that has changed color by absorbing the sebum on the skin. It is noted that the analyzing means 46 stores the above-described analysis results in the storage means 45.

The display screen generating means 47 generates a screen displaying analysis results obtained from the texture/pores, spots, skin tone, and sebum determination results, and the output means 42 outputs the generated screen so that a counselor or a doctor may make relevant evaluations. Specifically, the display screen generating means 47 generates a screen that displays a value representing the skin texture/pores, an image of spots, a value representing the skin tone, and a value representing the amount of sebum, and the generated screen is displayed by the output means 42. Further, in addition to displaying the latest images and analyses related to skin texture/pores, skin tone, and sebum, the screen generated by the screen generating means 47 may display at least one set of such images and analyses of the same skin area of the same member obtained in a previous examination which information is stored in the storage means 45. Also, in addition to displaying the latest image of spots, the screen generated by the screen generating means 47 may display at least one image of spots of the same skin area of the same member obtained in a previous examination which information is stored in the storage means 45.

The display screen generating means 47 may also perform a process of generating distribution data related to skin texture/pores, spots, skin tone, and sebum for different ages based on previously accumulated data, and displaying the examination data of an examinee on the distribution data. In this way, relative evaluation according to different ages (e.g., age groups, generations) may be possible. Further, the display screen generating means 47 may generate a screen displaying previous examination results in time-series (in chronological order) as progressive data. In this way, the change in the skin state with respect to elapsed time may be determined and the future state of the skin may be estimated with accuracy.

The display screen generating means 47 may prompt the user (e.g., counselor) to select from the displayed screen, via the input means 41, for example, a region that is to be evaluated. In turn, the analyzing means 46 may perform relevant analyses such as RGB value or HLS value determination on the selected region after which a screen may be regenerated and displayed.

For example, in the case of analyzing spots, first, an analyzing region within an image is designated and the R value (red), G value (green), B value (blue), H value (hue), L value (luminosity), and S value (saturation) of the region are determined. Then, the determination results are displayed along with previous determination results so that changes in color and brightness may be determined and accurate evaluation of spots may be enabled. It is noted that exemplary output screens generated by the display screen generating means 47 are described below.

The control means 48 controls overall operations of the component elements of the skin state analyzing apparatus 12. Specifically, the control means 48 may control the transmission/reception means 44 to receive information such as member information and/or determination information from the skin observing apparatus 11 based on instructions input via the input means 41, control the storage means 45 to store various types of information, and control processes such as analyzing, displaying, and outputting the determination information, for example.

<Numerical Analysis of Skin Texture/Pores by Analyzing Means 46>

Figure 4:
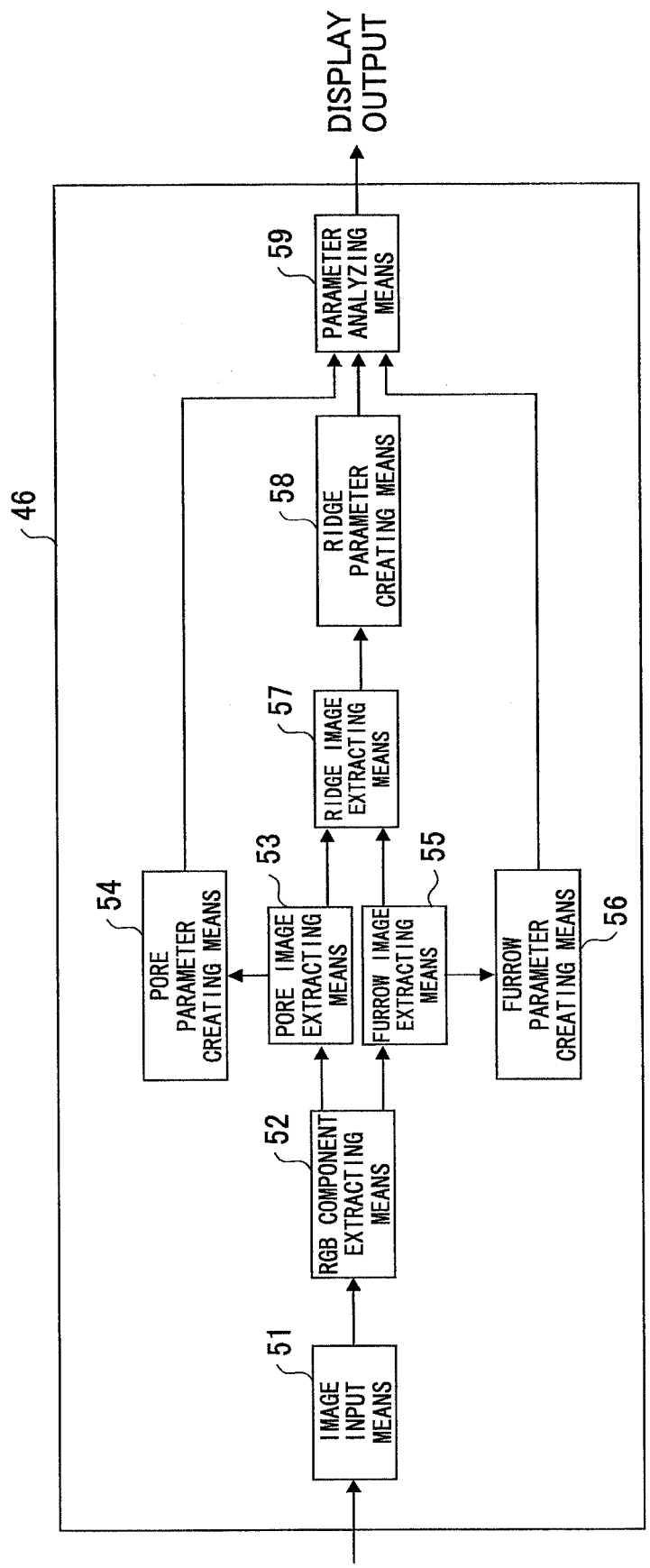
FIG. 4 is a diagram showing an exemplary configuration of analyzing means for representing skin texture/pores by numerical values.

In the following, a numerical analysis method for analyzing the skin texture/pores by the analyzing means 46 is described. FIG. 4 is a diagram showing an exemplary configuration of the analyzing means 46 for implementing the numerical analysis method for analyzing the skin texture/pores. According to FIG. 4, the analyzing means 46 includes image input means 51, RGB component extracting means 52, pore image extracting means 53, pore parameter generating means 54, furrow image extracting means 55, furrow parameter generating means 56, ridge image extracting means 57, ridge parameter generating means 58, and parameter analyzing means 59.

The image input means 51 inputs an image from the skin observing apparatus 11. The input image may be an image captured by a high image quality camera, for example, or more preferably a high quality image captured by a microscope such as a video microscope (VMS). In a case where the image acquired by the image input means 51 is an image of the entire face, the image may be divided into predetermined image sizes (regions), and the divided images or one or more image regions selected from the divided images by a user may be input to the RGB component extracting means 52.

The RGB component extracting means 52 extracts the three primary color component images, namely, the R (red) component image, G (green) component image, and B (blue) component image, from the input image. Also, the RGB component extracting means 52 performs distortion correction on each of the R, G, and B components. In one example, the distortion correction of the RGB components may be performed using a Gaussian filter. Also, the RGB component extracting means 52 outputs the R component image and the B component or G component image to the pore image extracting means 53. Also, the RGB component extracting means 52 outputs a component image (e.g., G component image) used for extracting a furrow image to the furrow image extracting means 55.

The pore image extracting means 53 extracts a pore image from the R component image and B component or G component image acquired from the RGB component extracting means 52. Specifically, the pore image extracting means 53 may generate a differential image of the R component and the B component, binarize the generated differential image, and perform a smoothing process on the binarized image to extract the pore image, for example. It is noted that a differential image obtained by subtracting the B component from the R component (R-B image) is preferably used; however, the opposite differential image (B-R image) may be used as well.

In another example, the pore image extracting means 53 may generate a differential image of the R component and G component, binarize the generated differential image, and perform a smoothing process on the binarized image to extract the pore image. It is noted that it is easier to extract the pore image from the differential image of the R component and the B component owing to its higher contrast. Also in the examples described below, the differential image of the R component and the B component are used to extract the pore image. However, the present invention is not limited to such examples, and the differential image of the R component and the G component may be used as well. The pore image extracting means 53 outputs the extracted pore image to the pore parameter generating means 54 and the ridge image extracting means 57.

The pore parameter generating means 54 calculates the pore size based on the pore image, and generated a parameter based on the calculation result. Also, the pore parameter generating means 54 outputs the generated pore parameter to the parameter analyzing means 59.

The furrow image extracting means 55 performs noise removal on the input G component image. Also, the furrow image extracting means 55 performs relevant processes such as a differentiation process on the noise-removed image using a Gaussian filter and a binarization process on the differentiated image to extract a furrow image. It is noted that the furrow image extracting means 55 is not limited to extracting the furrow image from the G component image and may also extract the furrow image from the R component image, the G component image, or a composite image of two or more of the R, G, B component images.

Further, the furrow image extracting means 55 outputs the furrow image to the furrow parameter generating means 56 and the ridge image extracting means 57. The furrow parameter generating means 56 calculates a parameter related to furrow width. Also, the furrow parameter generating means 56 outputs the generated sulcus parameter to the parameter analyzing means 59.

The ridge image extracting means 57 extracts a ridge image based on the images obtained from the pore image extracting means 53 and the furrow image extracting means 55. Specifically, black/white inversion is performed on the image obtained from the furrow image extracting means 55, and the image obtained from the pore extracting means 53 is used to remove the pore portions of the image to conduct a noise removal process and extract the ridge image. Further, the ridge image extracting means 57 outputs the extracted ridge image to the ridge parameter generating means 58. The ridge parameter generating means 58 generates parameters related to the fineness and shape of the ridge. Also, the ridge parameter generating means 58 outputs the generated parameter to the parameter analyzing means 59.

The parameter analyzing means 59 analyzes the skin state based on at least one of the parameters obtained from the pore parameter generating means 54, the furrow parameter generating means 56, or the ridge parameter generating means 58. It is noted that the parameter analyzing means 59 may have the output means 42 display at least one of the pore parameter, the furrow parameter, the ridge parameter, the pore image, the furrow image, or the ridge image in a different color and display adjacent pores, furrows, and ridges in different colors. In this way, different pore portions, furrow portions, and ridge portion may be displayed in a visibly distinguishable manner. Therefore, the user and/or the examinee may easily determine the shapes and sizes of pores and ridges, for example. In other examples, hatchings or gratings may be used instead of different colors to distinguish a certain portion.

In this way, the skin state, especially the skin texture/pores of a examinee may be accurately analyzed base on at least one of the information items (parameters) on pore size, furrow width, ridge fineness, or ridge shape.

It is noted that the above-described skin state analyzing apparatus 12 may be realized by a dedicated apparatus having the above-described functions, for example. In another example, a computer-executable program for enabling a computer to perform the above-described functions may be generated and installed in a general purpose personal computer or server so that the skin state analyzing processes according to embodiments of the present invention may be performed.

<Hardware Configuration>

Figure 5:
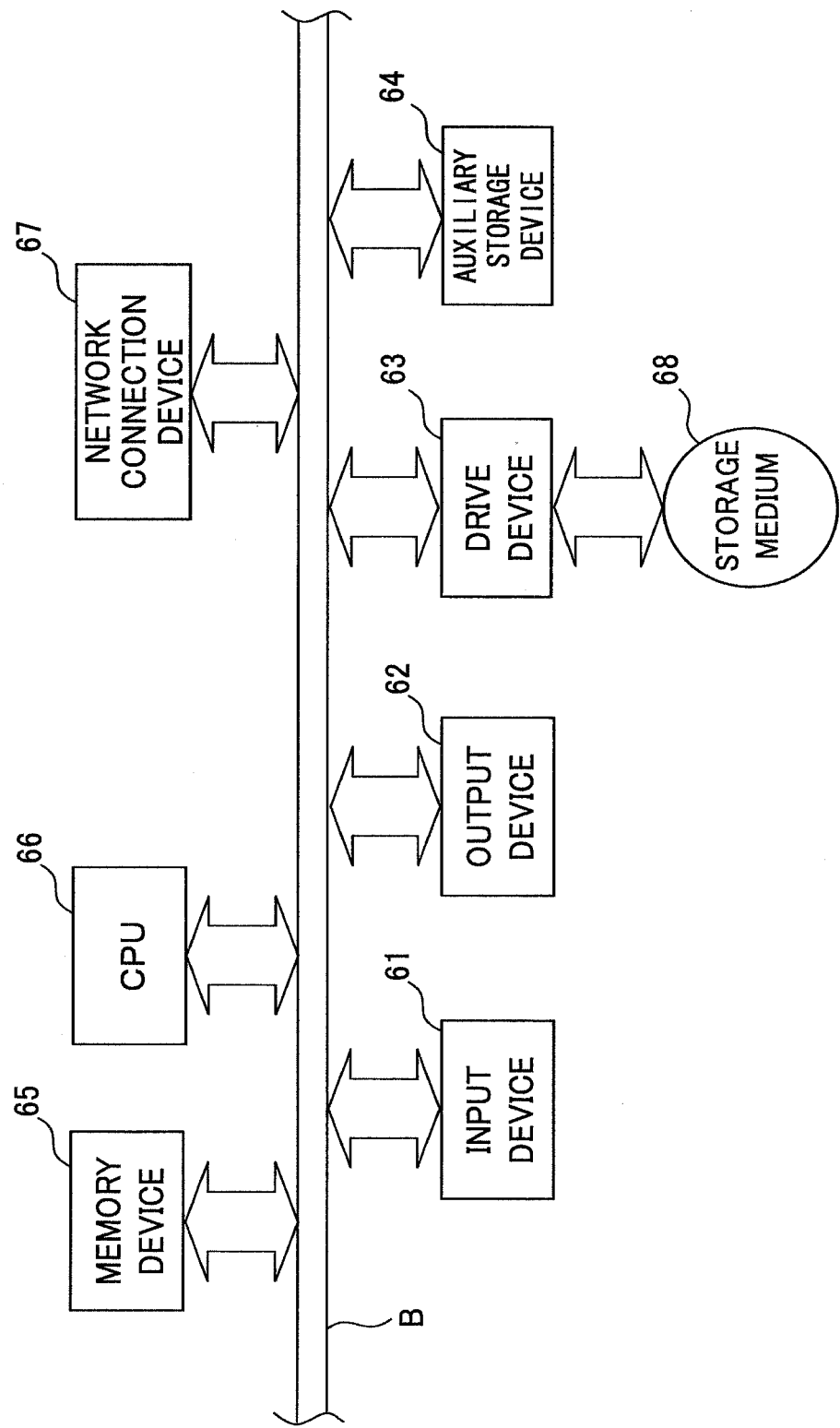
FIG. 5 is a diagram showing an exemplary hardware configuration in which skin state analysis according to an embodiment of the present invention may be performed.

In the following, a hardware configuration of a computer that is capable of executing skin state analysis according to an embodiment of the present invention is described. FIG. 5 is a diagram showing an exemplary hardware configuration for performing skin state analysis according to an embodiment of the present invention.

A computer mainframe shown in FIG. 5 includes an input device 61, an output device 62, a drive device 63, an auxiliary storage device 64, a memory device 65, a CPU (Central Processing Unit) 66 for performing various control operations, and a network connection device 67, and these components are interconnected by a system bus B.

The input device 61 may include a keyboard and a pointing device such as a mouse that are operated by the user. The input device inputs operation signals such as program execution command signals from the user. The output device 62 includes a monitor for displaying data and windows for operating the computer mainframe to perform processes according to embodiments of the present invention. It is noted that the execution progress and results of a relevant program may be displayed by the output means 62 according to a control program of the CPU 66.

The execution program to be installed in the computer mainframe may be stored in a storage medium 68 such as a CD-ROM. The storage medium 68 storing such a program may be set to the drive device 63, and the execution program stored in the storage medium 68 may be installed in the auxiliary storage device 64 via the drive device 63.

The auxiliary storage device 64 corresponds to storage means such as a hard disk that stores relevant programs such as execution programs and control programs that may be input/output as is necessary or desired.

The CPU 66 enables execution of skin state analyzing processes by controlling overall operations of the computer such as data input/output operations between various computations and hardware components based on a control program such as an OS (operating system) and an execution program read and stored by the memory device 65, for example. It is noted that information such as skin state determination results that are to be used during program execution may be obtained from the auxiliary storage device 64, and execution results may be stored therein.

The network connection device 67 may establish connection with the communications network 13, for example, to acquire an execution program from another terminal connected to the communications network 13 or transmit execution results obtained by executing a program or the execution program itself to another termination connected to the communications network 13. It is noted that processes related to skin state analysis an embodiment of the present invention may be executed by the above-described hardware configuration. Also, it is noted that the skin state analysis according to an embodiment of the present invention may be easily executed by a general purpose personal computer, for example, by installing a relevant program therein. In the following, specific descriptions of skin state analyzing processes are given.

<Skin State Analyzing Process Steps>

Figure 6:
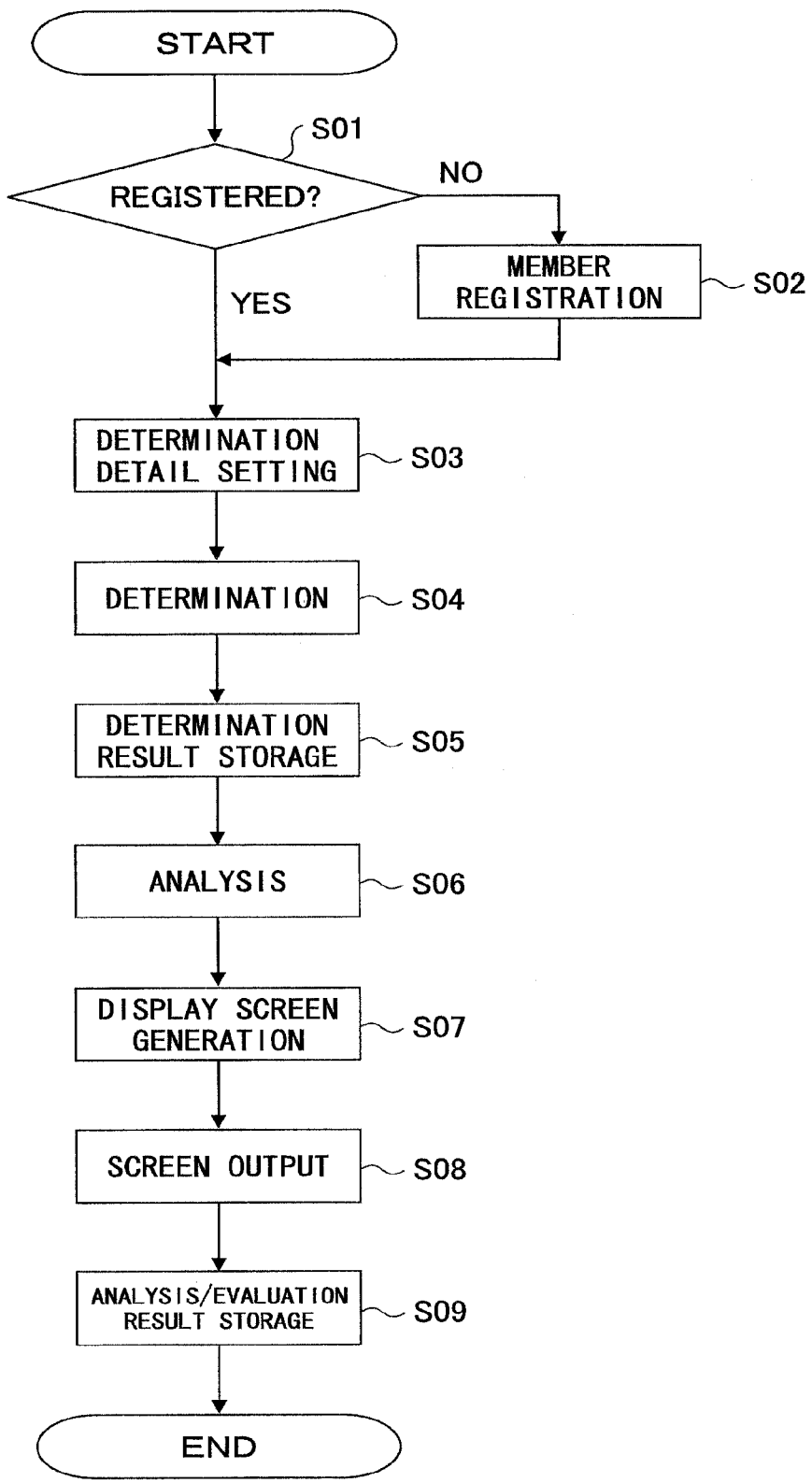
FIG. 6 is a flowchart illustrating exemplary skin state analyzing process steps according to an embodiment of the present invention.

In the following, process steps of a skin state analyzing system according to an embodiment of the present invention are described. FIG. 6 is a flowchart showing exemplary process steps of a skin state analyzing system according to an embodiment of the present invention. It is noted that the flowchart of FIG. 6 illustrates process steps of the skin state analyzing system including the skin observing apparatus 11 and the skin state analyzing apparatus 12.

According to FIG. 6, to conduct skin analysis, first, a determination is made as to whether the examinee is a registered member (S01). If the examinee is not a registered member (S01, NO), member registration of the examinee is performed (S02). It is noted that member information to be registered may include information on items such as "file number", "name", "date of birth", "gender", "examination area", and "memo (remarks)" for identifying each examination entry, for example, as is described above in relation to the member management means 23. However, member information to be registered is not limited to any particular type of information, and in another example, information on "age group" may be registered instead of the information item "date of birth".

Also, in determining whether the examinee is a registered member in step S01, an inquiry may be made as to whether member information on the examinee is registered by searching information stored in the storage means 25 using the information item "file number" or "name", for example.

Also, after performing member registration in step S02, or confirming that member information is already registered (S01, YES), determination details are set (step S03). Specifically, information specifying at least one of skin texture/pores, spots, skin tone, or sebum determination is acquired.

Then, determination is made based on the determination detail information acquired in step S03 (step S04). It is noted that the determination may be made by the skin observing apparatus 11 in the manner described above. Also, when performing the determination, the determination time/date is acquired, and the determination result is stored along with the acquired time/date information and the member information (step S05). By storing the determination result along with the time/date information, progressive display of determination results of the examinee may be enabled in an evaluation process described blow. In this way, multidimensional skin state analysis and evaluation may be performed.

Then, analysis of at least one of skin texture/pores, spots, or skin tone is performed based on the determination result (step S06) after which a display screen is generated that includes images representing the determination result and the analysis result according to predetermined conditions (step S07). The display screen generated in step S07 is displayed by a display or some other output means to present relevant information to the examiner (e.g., doctor) and/or the examinee (step S08). Also, the determination result and the analysis result are stored (step S09) so that the system process may be ended. It is noted that the process steps S01 through S09 may be subdivided into a skin observing process (S01-S05) and a skin state analyzing process (step S06-S09) corresponding to separate programs that may be individually installed in separate apparatuses or the same apparatus, for example. Specifically, the process steps S01-S05 may be performed in the case of merely determining the state of the skin, and the process steps S06-S09 may be performed when determination results are already registered, for example.

As can be appreciated from the above descriptions, by performing a skin state analyzing process according to an embodiment of the present invention, multidimensional skin state analysis may be accurately performed based on calculated values, image observations as well as evaluations in relation to age distribution or time distribution, for example.

<S06: Analysis>

Figure 7:
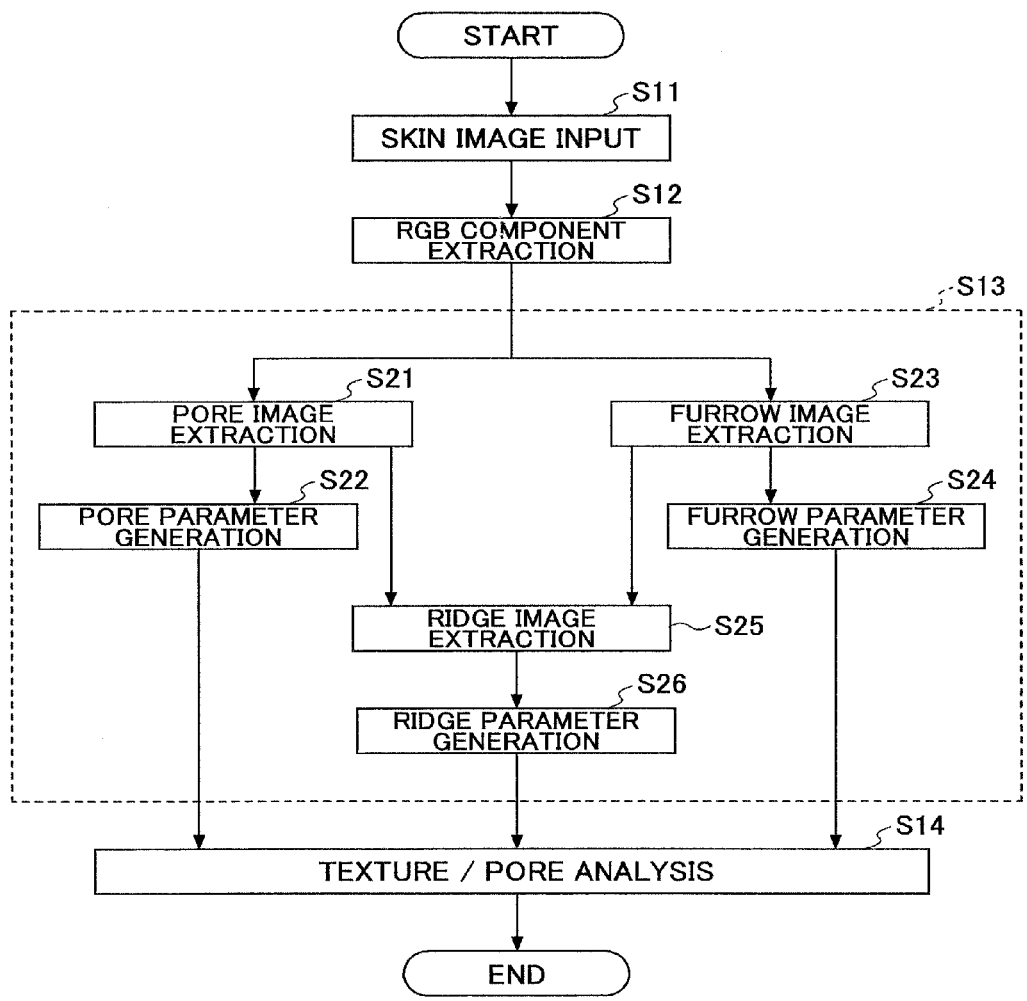
FIG. 7 is a flowchart illustrating exemplary process steps for analyzing the skin texture/pores.

In the following, analysis process steps for analyzing the skin texture/pores of the above-described analysis processes are described in detail. FIG. 7 is a flowchart illustrating exemplary process steps for analyzing the skin texture/pores.

According to the flowchart of FIG. 7, first, a skin image stored in step S05 is input (step S11) and RGB component extraction is performed thereon (step S12). In the following descriptions, it is assumed that the image input as an original image corresponds to a sectional image of the skin that may be acquired by a VMS as is described above, for example. However, in other examples, an image of the entire face of the examinee may be used. In this case, the image may be divided into predetermined image regions and RGB component extraction may be performed on each of these divided image regions, for example.

Next, in step S12, the extracted R, G, and B component images are used to parameterize at least one of the pore size, furrow width, ridge fineness, or ridge shape (step S13). Then, at least one of the parameters generated in step S13 is used to analyze the skin texture or pores based on the skin image input in step S11 (step S14).

As is shown in FIG. 7, the parameter generating step may involve using the R, G, and B component images acquired in step S12 to extract a pore image (step S21), parameterizing the pore size based on the extracted pore image using a numerical value, for example, and generating a pore parameter (step S22).

The parameter generating step S13 may also involve using the R, G, and B component images acquired in step S12 to extract a furrow image (step S23), parameterizing the furrow width based on the extracted furrow image using a numerical value, for example, and generating a furrow parameter (step S24). It is noted that the furrow width may be expressed by the width of a furrow within a predetermined image size, for example.

The parameter generating step S13 may further involve using the pore image acquired in step S21 and the furrow image acquired in step S23 to extract a ridge image (step S25), parameterizing the ridge fineness and the ridge shape based on the extracted ridge image using numerical values, for example, and generating a ridge parameter (step S26).

In step S14, the pore parameter, the furrow parameter, the ridge parameter, and at least one of the pore image, the furrow image, and the ridge image may be displayed using different colors. More specifically, adjacent pores, furrows and ridges may be displayed in different colors so that different pore portions, furrow portions, and ridge portions may be displayed in a visually distinguishable manner. In this way, a user may be able to easily determine the shapes, sizes, and numbers of pores, furrows, and ridges, for example. In other examples, hatchings and gratings may be used to enable easy determination of what is being represented.

<Pore Image Extraction, Pore Parameter Generation>

Figure 8:
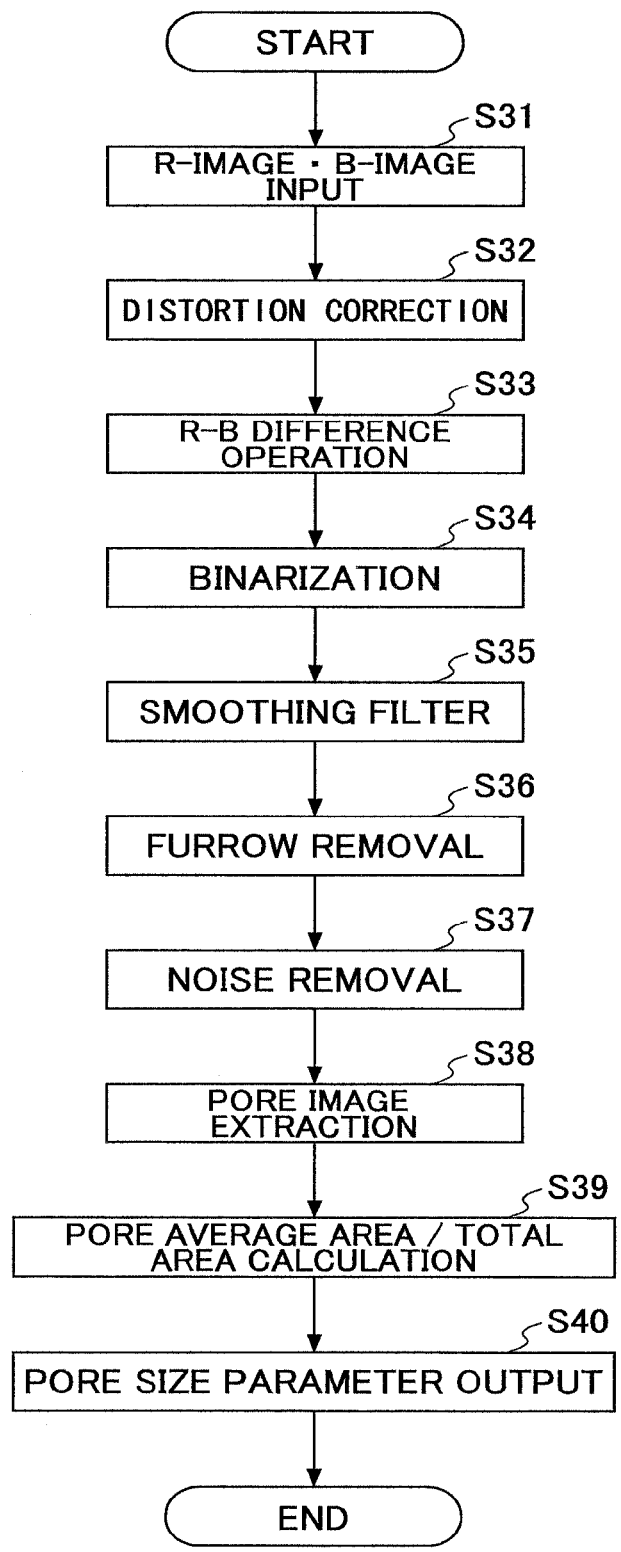
FIG. 8 is a flowchart illustrating exemplary process steps for pore image extraction and pore parameter generation according to an embodiment of the present invention.
Figure 9:
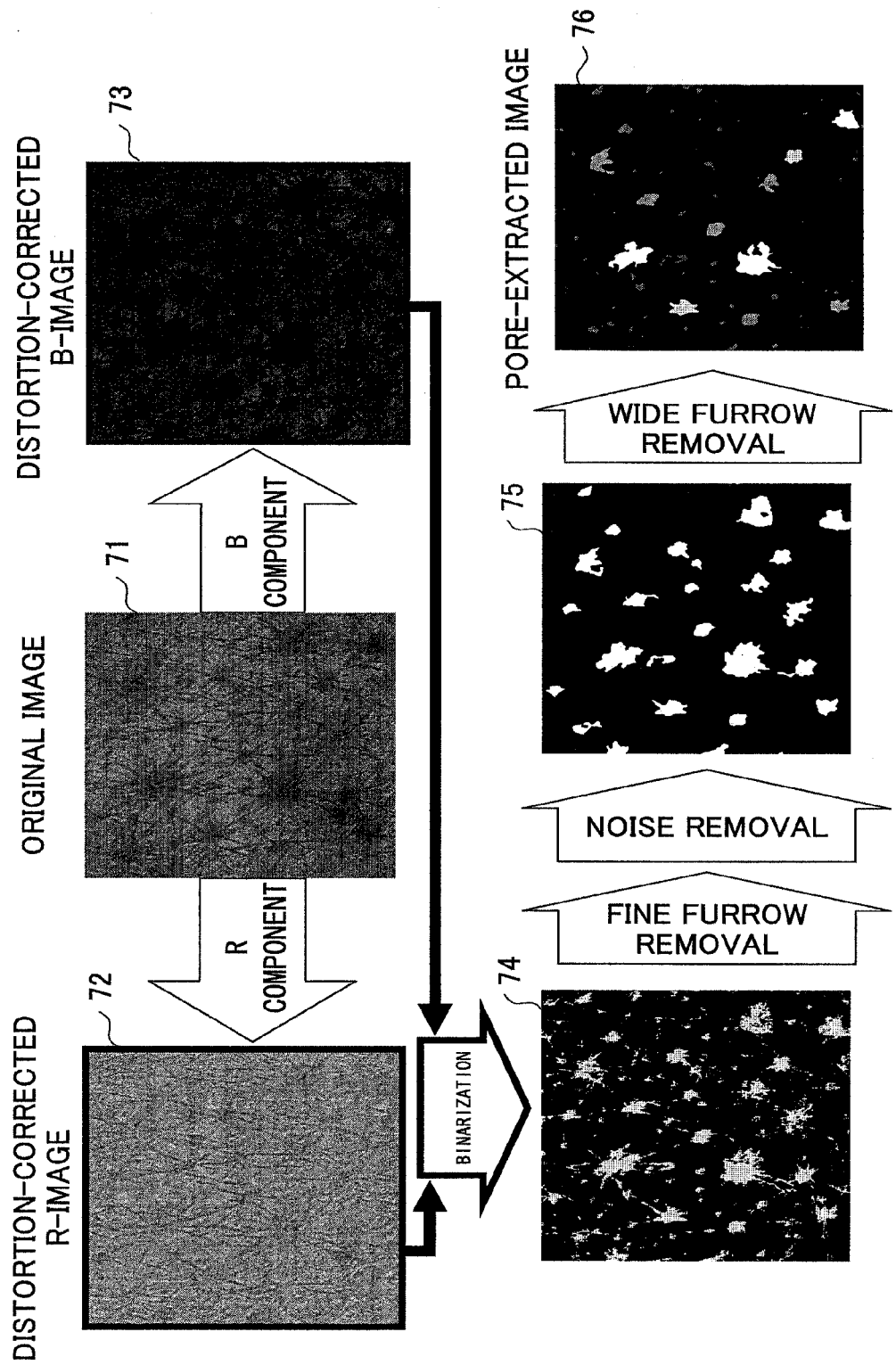
FIG. 9 is a diagram showing exemplary images that may be obtained during the pore image extraction process.

In the following, pore image extraction and pore parameter generation of the above-described process steps S21 and S22 are described in detail. FIG. 8 is a flowchart illustrating process steps for pore image extraction and pore parameter generation according to an embodiment of the present invention. FIG. 9 is a diagram showing exemplary images that may be obtained in during the pore image extraction process.

According to the flowchart of FIG. 8, the R-image and the B-image extracted from the above-described process of extracting RGB components from an original image corresponding to the input image (e.g., original image 71 of FIG. 9) are input (step S31). Then, distortion correction is performed on the input images using a Gaussian filter, for example, in order to remove distortions at peripheral portions of the input images (step S32).

In the present example, it is assumed that the distortion correction is performed using a Gaussian filter as a smoothing filter. It is noted that in a smoothing filter such as the Gaussian filter, when the cutoff frequency is set relatively high distortions may not be adequately corrected, and when the cutoff frequency is set relatively low, although distortions may be corrected image portions representing the skin texture may be removed through correction along with the distortions. Thus, the cutoff frequency is preferably set to a suitable value based on factors such as the magnification and resolution of the skin image. For example, if the input image corresponds to an 8-bit image of 640×480 pixels captured using a microscope with a magnification of 50 times, the cutoff frequency of the Gaussian filter is preferably set to 1.6-1.8 mm.

Next, using the distortion corrected images (e.g., R-image 72 and B-image 73 of FIG. 9), a differential operation is performed on the R-image and the B-image to emphasize the pores (step S33). Although the difference operation to be performed may vary depending on the images used, in one example, the formula "R−B*R_ave/B_ave×a" may be used the R−B difference operation formula. In this formula, "R_ave" denotes the average value of the R component, and "B_ave" denotes the average value of the B component. Also, "a" denotes a value that may be arbitrarily set depending on the image size and the resolution of the skin image, for example. In a preferred embodiment, the value of "a" is preferably within 1.3-1.5.

Then, the calculated R-B difference image is binarized (e.g., image 74 of FIG. 9) in order to extract pore portions (step S34). Further, fine furrows are removed from the R−B difference image obtained in step S34 through noise removal, and compensation of the noise removed portions is performed (step S35). Specifically, a smoothing process may be performed using a median filter, for example. In this case, the filtering process may involve successively performing 1-10 rounds of shrinking and expanding operations on a 3×3 pixel rectangular image, or successively performing 1-5 rounds of shrinking and expanding operations on a 5×5 pixel rectangular image to filter fine furrows, for example. In this way, fine furrow portions may be removed (step S36). It is noted that in an alternative embodiment, a R−G difference image may be used in place of the R−B difference image as is described above.

By performing the above-described processes to have furrows of a certain size or greater subject to skin state analysis, errors due to fine furrows or noise may be removed so that accurate skin state analysis may be consistently performed.

Also, the image extracted in step S36 by having fine furrows removed therefrom may be used to remove noise by performing a labeling process on each furrow (step S37). Further, wide furrow portions may be removed from the image obtained in step S37 (e.g., image 75 of FIG. 9) to obtain a pore extracted image (e.g., image 76 of FIG. 9) (step S38). It is noted that the noise removal process of step S37 may be performed using a norm of 50-400 pixels (0.005-0.04 mm$^2$) or less, for example, extracting pore portions that are larger than the norm and removing other pore portions and furrows.

In the pore parameter generation process according to the present embodiment, the average pore area is used as a reference index for determining the pore size to be used as the pore parameter. Specifically, the average area or the total are of pores within a predetermined image region is calculated (step S39), and the calculated area is used as a reference index to generate and output a pore size parameter (S40).

<Furrow Extraction, Furrow Parameter Generation>

Figure 10:
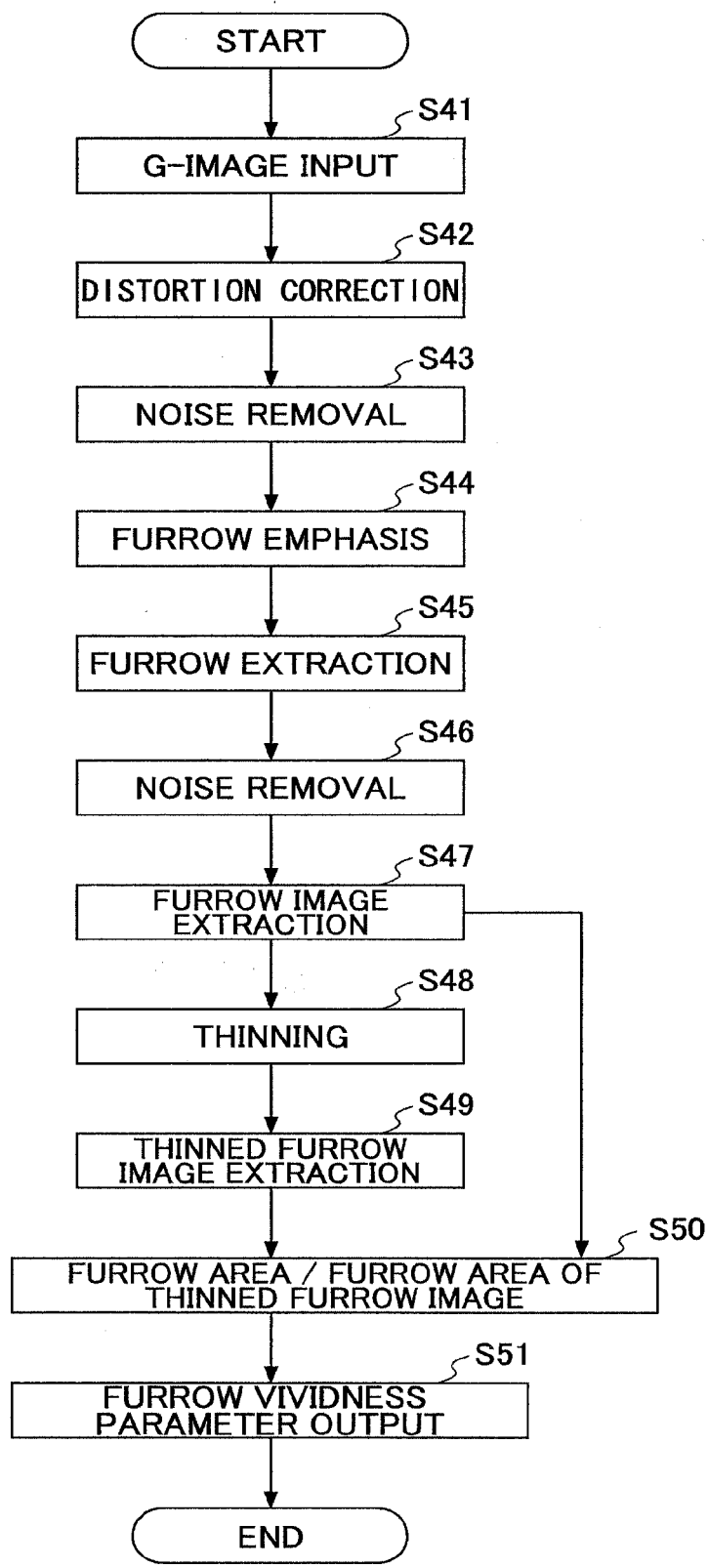
FIG. 10 is a flowchart illustrating exemplary process steps for furrow image extraction and furrow parameter generation according to an embodiment of the present invention.
Figure 11:
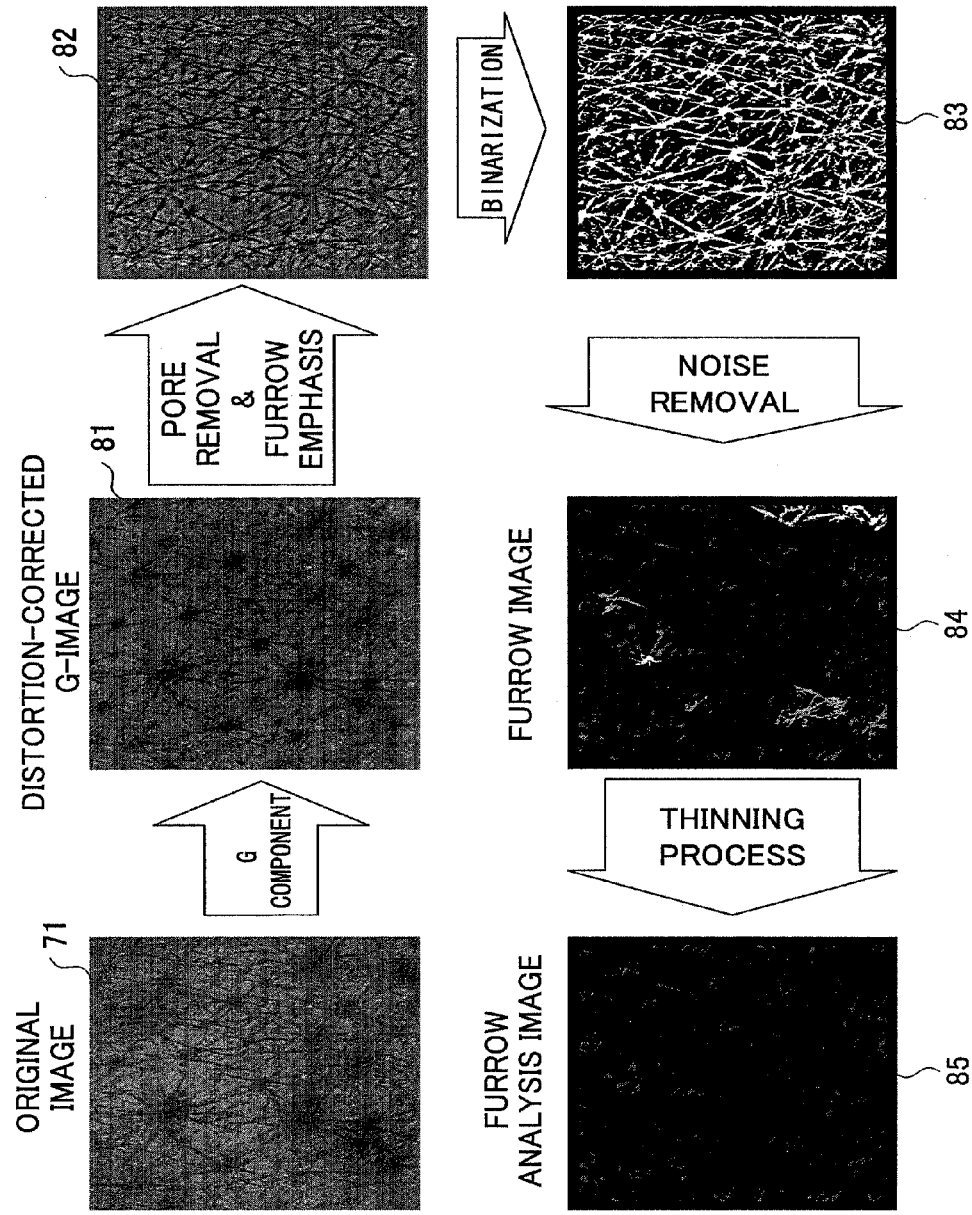
FIG. 11 is a diagram showing exemplary images that may be obtained during the furrow image extraction process.

In the following, furrow image extraction and furrow parameter generation of the above-described process steps S23 and S24 are described in detail. FIG. 10 is a flowchart illustrating process steps for furrow image extraction and furrow parameter generation according an embodiment of the present invention. FIG. 11 is a diagram showing exemplary images that may be obtained during the furrow image extraction process.

According to the flowchart of FIG. 10, the R-image and the B-image extracted from the above-described process of extracting RGB components from an original image corresponding to the input image (e.g., original image 71 of FIG. 11) are input (step S41). Then, distortion correction is performed on the input images using a Gaussian filter, for example, in order to remove distortions at peripheral portions of the input images (step S42). For example, if the input image corresponds to an 8-bit image of 640×480 pixels captured using a microscope with a magnification of 50 times, image filtering may be performed setting the cutoff frequency of the Gaussian filter to 1.6-1.8 mm.

Next, noise removal is performed on the distortion corrected images (e.g., G-image 81 of FIG. 11) (step S43). It is noted that this noise removal process may be performed using a smoothing filter. In this case, the smoothing filter may be cross-shaped and its size may be about 3×3 pixels (0.03×0.03 mm) to 5×5 pixels (0.05×0.05 mm), for example.

Next, a furrow emphasizing process is performed on the noise removed image using a differential filter (step S44). It is noted that the differential filter is preferably set to a suitable size according to the width and the distribution characteristics of the furrows, for example. Specifically, each pixel may be processed using a differential filter of a suitable size (e.g., 5×5 pixels (0.05×0.05 mm) to 45×45 pixels (0.45×0.45 mm). In this way, noise increase as a result of using a small size filter may be prevented and extraction or portions other than furrows such as pores as a result of using a large size filter may be prevented as well. In this way, an image including furrows that are emphasized and having pores removed may be obtained (e.g., image 82 of FIG. 11). Further, the image obtained in step S44 may be binarized to extract a furrow image (e.g., image 83 of FIG. 11) (step S45).

Also, the image extracted in step S45 may be used to perform a labeling process on each furrow to remove noise (step S46). Specifically, the noise removal may be preformed using a norm of 50-400 pixels (0.005-0.04 mm$^2$) or less, removing pores and furrows with predetermined widths as noise to extract a noise removed furrow image (e.g., image 84 of FIG. 11) (step S47).

Further, a thinning process is performed on the image obtained in step S47 (step S48) to extract a thinned furrow image (step S49).

Next, in the furrow parameter generation process according to the present embodiment, the average width of furrows within a predetermined image is used as a reference index in obtaining the furrow width to be used as the furrow parameter. Specifically, the area of furrows within the image obtained in step S47 is divided by the area of furrows within the thinned furrow image obtained in step S49 (furrow area/furrow area of thinned furrow image) (step S50), and the furrow width is parameterized using the calculated value to generate and output the furrow width parameter (step S51).

<Ridge Image Extraction, Ridge Parameter Generation>

Figure 12:
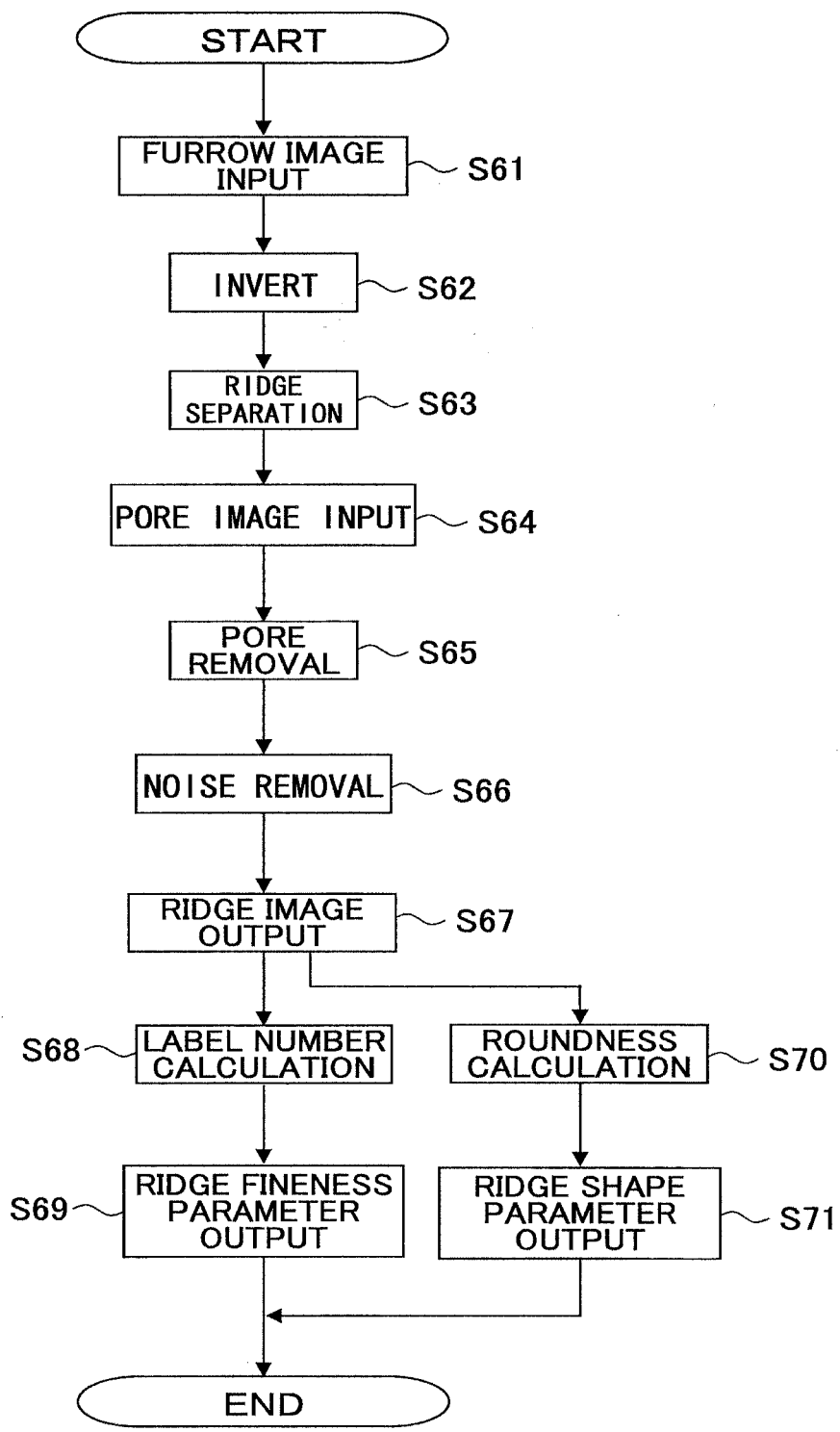
FIG. 12 is a flowchart illustrating exemplary process steps for ridge image extraction and ridge parameter generation according to an embodiment of the present invention.

In the following, ridge image extraction and ridge parameter generation of the above-described process steps S25 and S26 are described in detail. FIG. 12 is a flowchart illustrating process steps for ridge image extraction and ridge parameter generation according to an embodiment of the present invention. FIG. 13 is a diagram showing exemplary images that are extracted during the ridge image extraction process.

According to the flowchart of FIG. 12, the furrow image obtained in step S47 (e.g., image 91 of FIG. 13) is input (step S61). Then, a black-white inversion process is performed on the input furrow image and a labeling process is performed on each ridge within the inverted image to remove noise (step S62).

In the labeling process, plural ridges that are connected to one another may be labeled as one single ridge. However, since the number of ridges is used as a reference index in a subsequent process, labeling has to be accurately performed on each ridge. In this respect, a ridge separation process is performed on the image obtained in step S62 (e.g., image 92 in FIG. 13) (step S63).

Figure 14A:
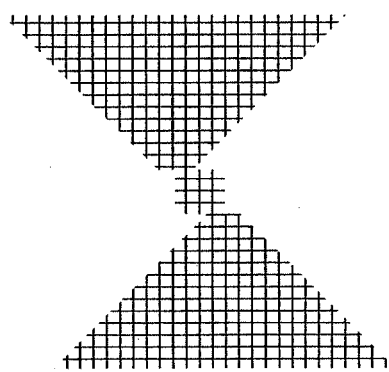
FIGS. 14A and 14B are diagrams illustrating a process of separating ridges within an image.
Figure 14B:
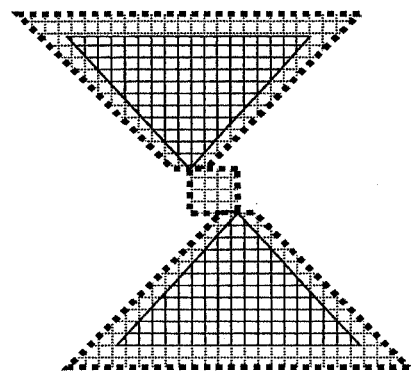

Specifically, the periphery of each ridge in the image obtained in step S62 may be scaled down by a predetermined number of pixels (e.g. 1-2 pixels) to separate the ridges. FIGS. 14A and 14B are diagrams illustrating an example of separating a ridge within an image. As is shown in FIG. 14A, in the labeling process of step S62, plural ridges connected to one another may be labeled as one ridge. Accordingly, as is shown in FIG. 14B, the periphery of each labeled ridge image is scaled down by one pixel in order to obtain an image in which ridges are separated from each other (e.g., image 93 of FIG. 13). It is noted that the number of pixels by which the ridge image is scaled down is not limited to one pixel, and in other alternative examples, the periphery of the ridge image may be scaled down by two or three pixels.

Next, the pore image obtained in step S38 is input (step S64), and pore portions of the input pore image are removed (step S65). Specifically, a difference image between the ridge separated image extracted in step S63 and the pore image input in step S64 is obtained to generate a ridge analysis image (e.g., image 94 of FIG. 13).

Next, a labeling process is performed on each ridge to remove noise (step S66), and the noise removed image is output as a ridge image (step S67). In this case, noise removal may be performed using a norm of 1-100 pixels (0.001-0.01 mm$^2$) or less to obtain ridge images of a predetermined size.

Next, in the ridge parameter generation process according to the present embodiment, the ridge, the number of ridges or the average area of ridges within a predetermined image region such as the facial surface or a 100-cm$^2$ area may be used as a reference index for obtaining the ridge fineness to be used as the ridge parameter. Specifically, the label number is calculated from the ridge image obtained in step S67 (step S68). In this case, the label number represents the number of ridges that are labeled within the image. The number of ridges may be parameterized as the reference index of the ridge fineness using a numerical value and output (step S69). It is noted that the number of ridges may be calculated by counting the number of ridges within a 4.8 mm$^2$-image area, for example. However, the method of counting the number of ridges is not limited to such a method, and in other alternative example, the ridges may be counted manually from an image and calculated in accordance with the facial surface area.

In another example, the average area of ridges included within a predetermined image area may be calculated and the calculated value may be used to express the ridge fineness. In this case, the average area may be accorded with the facial surface area to calculate a total number of ridges, for example.

In the parameter generation process of the present embodiment, the ridge shape to be uses as another parameter aside from the ridge fineness may use the roundness of the ridges included within a predetermined image region as a reference index. Specifically, roundness of the ridges may be calculated from the ridge image obtained in step S67 (step S70), and the calculated roundness may be parameterized using a numerical value and output (step S71). It is noted that the roundness used in step S71 may be calculated by computing the formula "4π×ridge area/(ridge circumference×ridge circumference)" on the ridge image, for example. However, the method of calculating the roundness is by no means limited to such an example.

By using the above-described four parameters related to "pore size", "furrow width", "ridge fineness", and "ridge shape" as criteria (reference indexes) for analyzing the skin texture/pores, accurate skin stat analysis using numerical values may be performed.

Also, according to the above-described embodiment, the parameter related to "pore size" is generated based on the pore area obtained from the skin image, the parameter related to "furrow width" is generated based on the average width of furrows obtained from the skin image, the parameter related to "ridge fineness" is generated based on the number of ridge labels (number of ridges) obtained from the skin image, and the parameter related to "ridge shape" is generated based on the roundness or ridges obtained from the skin image. In this way, the accurate analysis of the skin texture/pores may be enabled. Therefore accurate skin state analysis based on various factors may be performed.

<Display Screen Examples>

In the following, display screen examples are described with reference to the accompanying drawings. It is noted that the display screens described below may be displayed by selecting relevant information from a main menu, for example. Also, it is noted that the displayed information items and display layout of the display screens are by no way limited to the examples described below.

<Member Management Screen>

Figure 15:
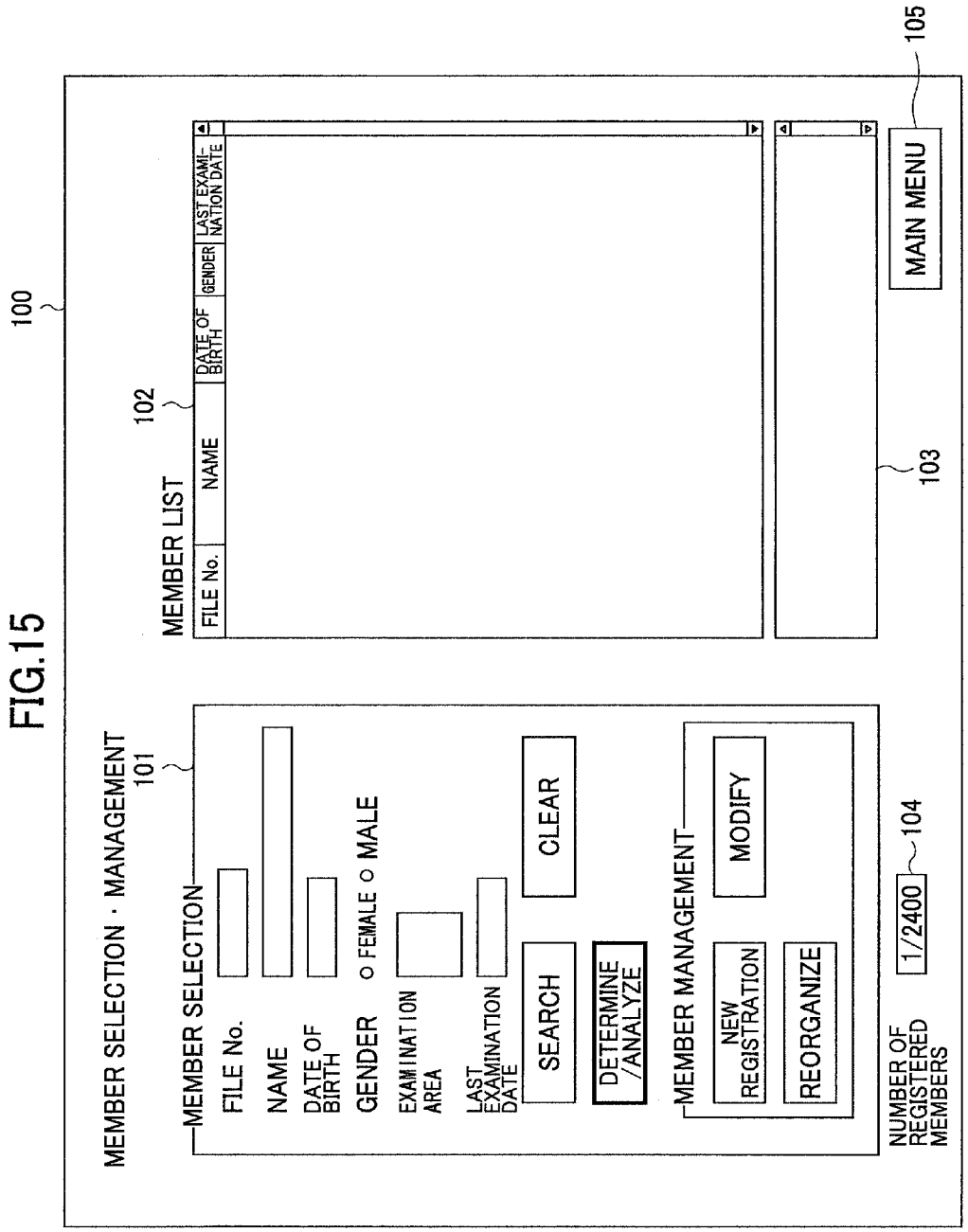
FIG. 15 is a diagram showing an exemplary member management screen.

FIG. 15 is a diagram showing an exemplary member management screen. The member management screen 100 shown in FIG. 15 includes a member selection area 101, a member list display area 102, and a remarks display area 103. In the member selection area, information for items such as "file number", "name", "gender", "date of birth", "examination area", "last examination date" may be input, for example. Also, the member selection area may include a "search" button, a "clear" button, a "determine/analyze" button, a "new registration" button, a "modify" button, and a "reorganize" button, for example.

First a determination is made as to whether member information of the examinee is stored in the member management database. For example, in FIG. 15, information for items such as "file number" and/or "name" may be input and the "search" button may be selected (clicked). If corresponding member information is registered, information for other items such as "gender", "date of birth", "examination area", and "last examination date" may be displayed so that a determination may be made as to whether such member information is registered. It is noted that the "clear" button may be used to clear the information for the items "file number" and/or "name". Also, the "determine/analyze" button may be selected in the case of actually performing determination or analysis of the skin state.

In the case where it is determined based on the search result that the examinee is not registered as a member, or member information of the examinee is not stored, a screen indicating a message informing of such a determination outcome may be displayed. In this case, new registration may be performed by inputting information for the above items "file number", "name", "gender", "date of birth", "examination area", "last examination date", and the remarks display area 103 so that the examinee may be registered as a new member. In turn, the registered member information may be displayed at the member list display area 102. It is noted that the registered member information may be modified by changing information for a predetermined item and selecting the "modify" button.

It is noted that the "reorganize" button may be used to transfer member information stored in the storage means to a CD-ROM or a DVD in a case where a registered member has not come to be examined for a relatively long time since his/her last examination, for example. Also, the member management screen 100 may include a registered member number display area 104 for displaying the number of registered member. In the case where a main menu is available, the member management screen 100 may include a main menu button for returning to the main menu.

<Examination Log Display Screen>

FIG. 16 is a diagram showing an exemplary examination log display screen. The examination log display screen 110 shown in FIG. 16 includes a member information display area 111 and an examination log display area 112. The member information display area displays information (e.g., "file number", "name", "date of birth", "examination area", etc.) on the member whose examination log is being displayed. The examination log display area 112 displays a list of past examination log entries that are identified by their "log number" assigned based on their examination date/time and their "examination date". The list includes columns for indicating whether each of determinations on the skin texture/pore, spots, skin tone, and sebum has been performed in each examination session. Specifically, the determination performed in an examination session is indicated by displaying a mark "●" in the corresponding column. In this way, it may be possible to easily determine when and what determinations have been performed so that the determinations to be performed in the present examination session may be decided based on the log information. It is noted that although the number of log entries to be stored for each member is not limited to a particular number, a predetermined limit (e.g., twelve log entries per member at the maximum) may be set according to certain embodiments.

<General Examination Result Display Screen>

Figure 17:
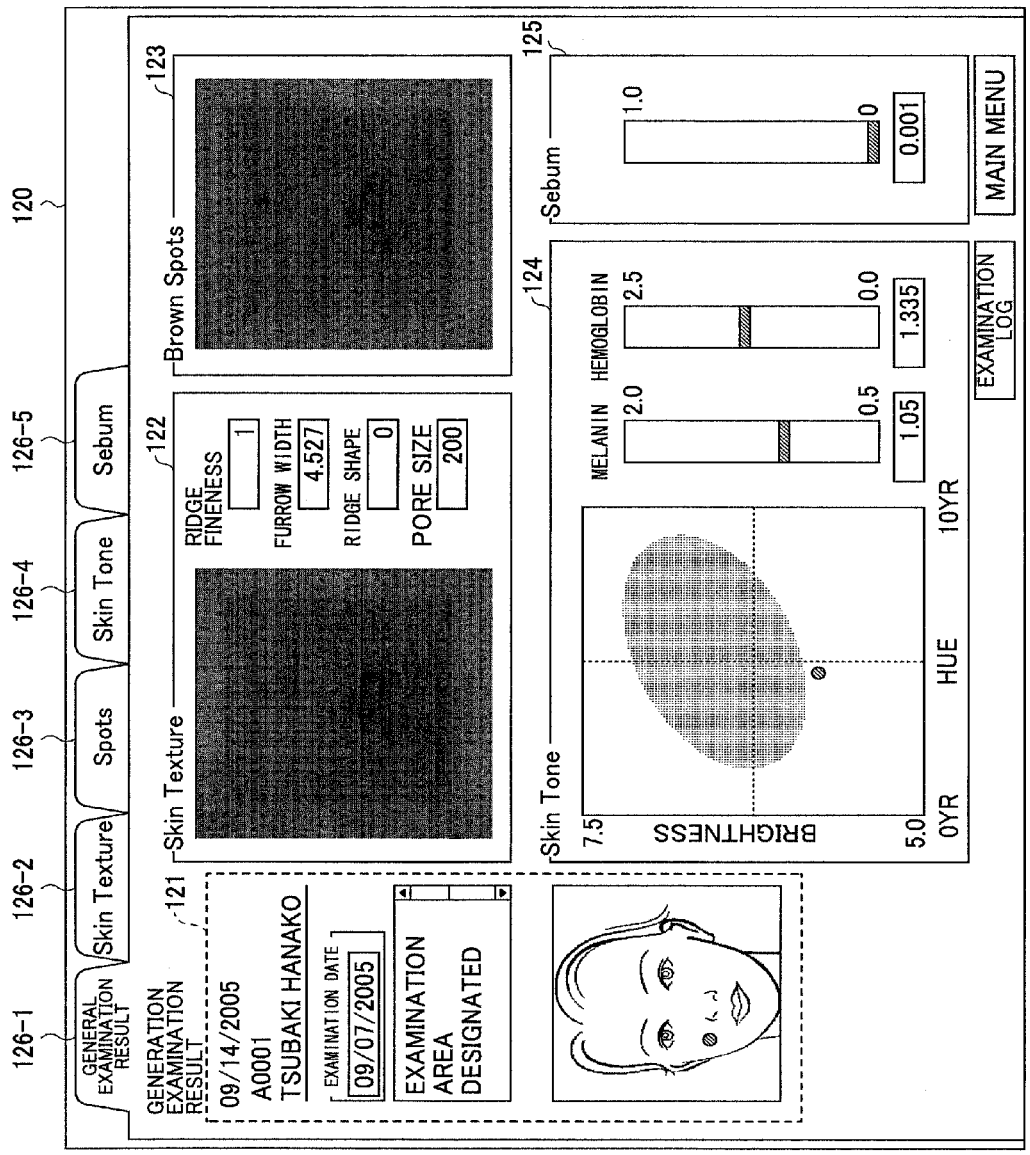
FIG. 17 is a diagram showing an exemplary general examination result display screen.

FIG. 17 is a diagram showing an exemplary general examination result display screen. The general examination result display screen 120 shown in FIG. 17 displays analyses of the determination results of the skin texture/pores, spots, skin tone, and sebum. Specifically, the general examination result display screen 120 includes a member information display area 121, a skin texture/pore analysis display area 122, a spots analysis display area 123, a skin tone analysis display area 124, and a sebum analysis display area 125. The member information display area 121 may display information items such as the result display date, file number, name, examination date, and remarks. The skin texture/pores analysis display area 122 may display an image of the skin texture/pores and information on ridge fineness, furrow width, and ridge shape, for example.

The spots analysis display area 123 may display an image of spot portions (e.g., localized image or enlarged localized image). The skin tone analysis display area 124 may display graphs representing the relationship between brightness and hue, the amount of melanin, and the amount of sebum of the examined skin. The sebum analysis display area 125 may display a value or a graph representing the amount of sebum, for example. It is noted that information items of the general examination result display screen 120 for displaying analysis information of determinations that have not been performed in the present examination may be left blank, for example.

Also, the general examination result display screen 120 includes tabs 126, namely, a general examination result tab 126-1, a skin texture/pores tab 126-2, a spots tab 126-3, a skin tone tab 126-4, and a sebum tab 126-5. By selecting the above tabs 126, detailed information of the corresponding determination/analysis items may be displayed. Also, the general examination result display screen 120 may include an examination log screen selection button for changing the display to the examination log display screen 110 shown in FIG. 16 buttons and/or a main menu button for changing the display to the main menu screen, for example.

<Skin Texture/Pores Display Screen>

Figure 18:
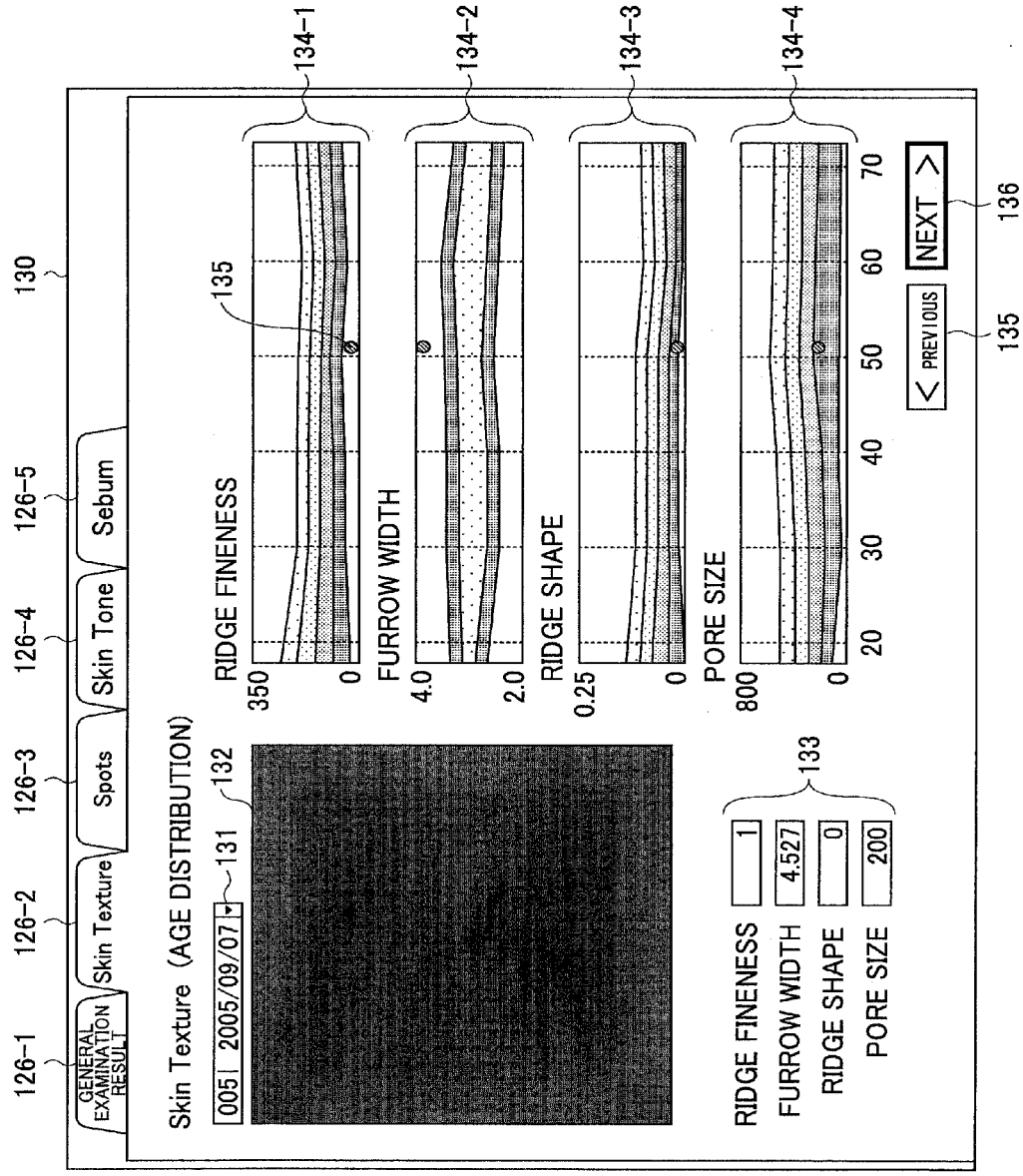
FIG. 18 is a diagram showing an exemplary skin texture/pores display screen.

FIG. 18 is a diagram showing an exemplary skin texture/pores display screen. The skin texture/pores display screen 130 shown in FIG. 18 includes an examination date selection part 131, an image display area 132, an analysis display area 133, and age distribution display areas 134-1 to 134-4 corresponding to the analysis items displayed. The examination date selection part 131 may be a combo box, for example, that enables selective display of skin texture/pores analyses of examination results of a desired examination date by selecting the desired examination date from examination log information including the present examination date and other previous examination dates.

When the desired examination date is selected via the examination selection part 131, a corresponding image is displayed on the image display area 132 and analysis results obtained by analyzing and numerically representing the ridge fineness, furrow width, ridge shape, and pore size are displayed at the analysis display region 133.

Further, the analysis results pertaining to the ridge fineness, furrow width, ridge shape, and pore size are represented in relation to the age of the examinee in the corresponding age distribution display areas 134-1 through 134-4. It is noted that the horizontal axes of the age distribution display areas 134-1 through 134-4 represent the age and the vertical axes represent the evaluation value. Also, it is noted that the age distribution display areas 134-1 through 134-4 each include one or more zones representing evaluation ranges used for classifying evaluation results. The zones may be evaluation result ranges that are set based on evaluation results according to age that are stored beforehand. For example, the zones may represent predetermined categories such as "good zone", "normal zone", "just a bit short zone", "try harder zone", "redness zone", and "yellowness zone". In this way, the analysis results of the examinee may be compared with data on the general skin states of persons in the same age group as the examinee to enable accurate analysis of the skin state according to the examinee.

It is noted that the zones may be displayed in different colors, or the zones may be displayed using hatchings and gratings, for example. Also, the zones are preferably defined using a predetermined function so that the zones may be accurately defined. For example, an "average value±standard deviation value" zone that represents the evaluation result range for 67% of persons in a relevant age group and an "average value±1.95×standard deviation value" zone that represents the evaluation result range for 95% of persons in the relevant age group may be separately defined and displayed.

It is noted that the skin texture/pores display screen 130 may also include a return button 135 and a next button 136, for example, so that the display may be switched to screens displaying the analysis results corresponding to the tabs 126-1 through 126-5 without having to select the tabs 126-1 through 126-5.

<Skin Texture/Pores Display Screen: Alternative Example>

Figure 19:
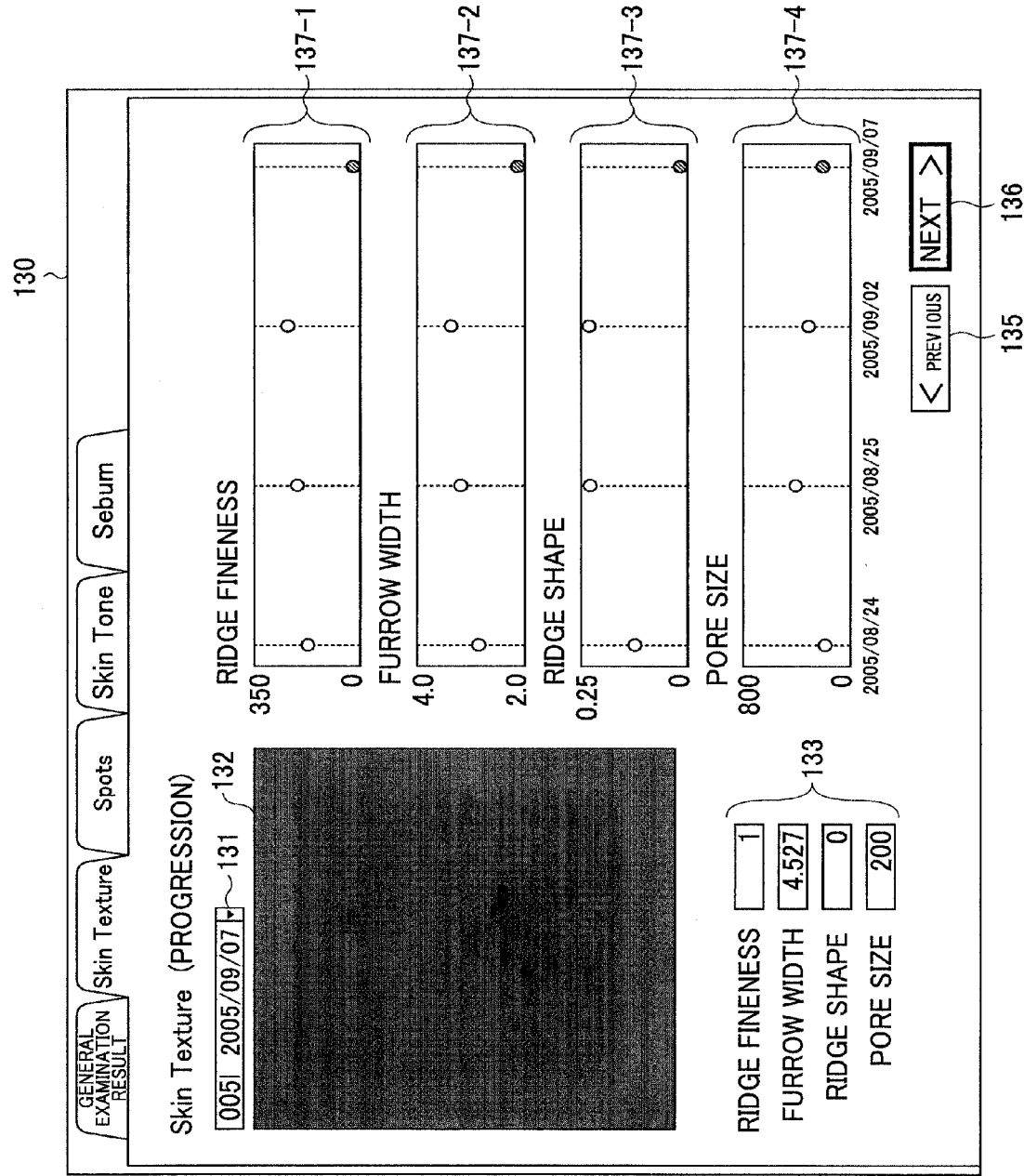
FIG. 19 is a diagram showing another exemplary skin texture/pores display screen.

FIG. 19 is a diagram showing another exemplary skin texture/pores display screen. In the skin texture/pores display screen of FIG. 19, examination progression display areas 137-1 through 137-4 are displayed in place of the age distribution display areas 134-1 through 134-4 so that other log information may be viewed as well. It is noted that the horizontal axes of the examination progression display areas 137-1 through 137-4 represent the date and the vertical axes represent the analysis value. It is noted that in FIG. 19, the horizontal axes of the examination progression display areas 137-1 through 137-4 representing the date are equidistantly divided by the number of examinations performed; however, the present invention is not limited to such an example, and in other examples, scales may be marked based on time length and the skin state at a date on which examination is not performed may be estimated based on examination results obtained before and after this date. In this way, the progressive state of the skin may be analyzed and estimations may be accurately made with regard to the future state of the skin. Also, it is noted that the skin texture/pore display screen is not limited to the examples described above and in other examples, both the age distribution display areas 134 and the examination progression display areas 137 may be displayed within one screen.

<Spots Display Screen>

Figure 20:
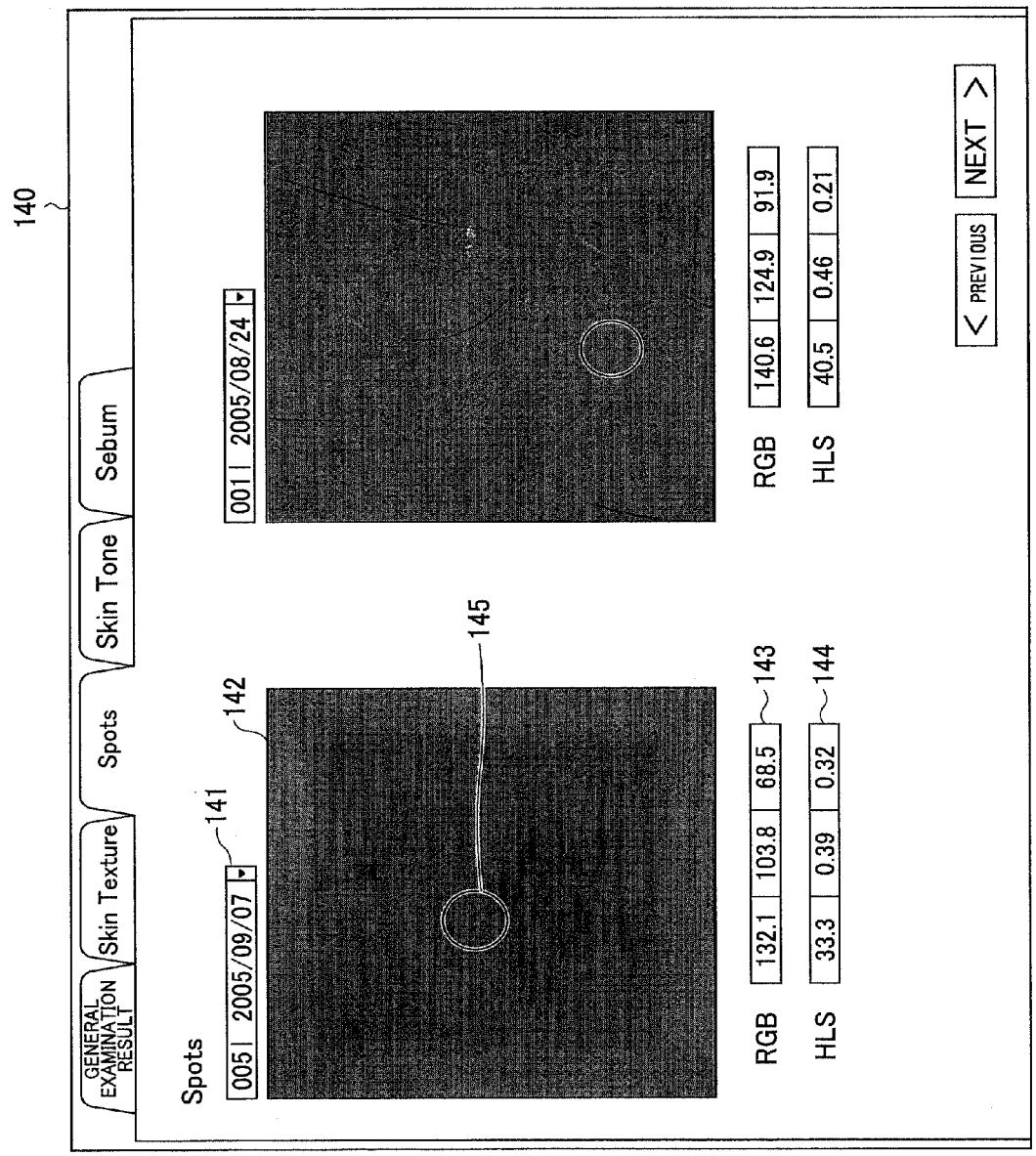
FIG. 20 is a diagram showing an exemplary spots display screen.

FIG. 20 is a diagram showing an exemplary spots display screen. The spots display screen 140 shown in FIG. 20 includes an examination date selection part 141, an image display area 142, an RGB value display part 143, and an HLS value display part 144. A predetermined location containing spots, for example, may be selected from the image displayed on the image display area 142 so that corresponding RGB values and HLS values of a circular region 145 centered around the selected location and having a predetermined diameter may be displayed at the RGB value display part 143 and the HLS value display part 144, respectively. It is noted that the region 145 is not limited to being circular, and in other examples, the region 145 may be arranged into an ellipse shape or a polygon shape.

Also, it is noted that the spots display screen 140 may display plural evaluation results selected from the examination log. In this way, progressive evaluation of spots may be possible by based on the contents of one display screen.

<Skin Tone Display Screen>

Figure 21:
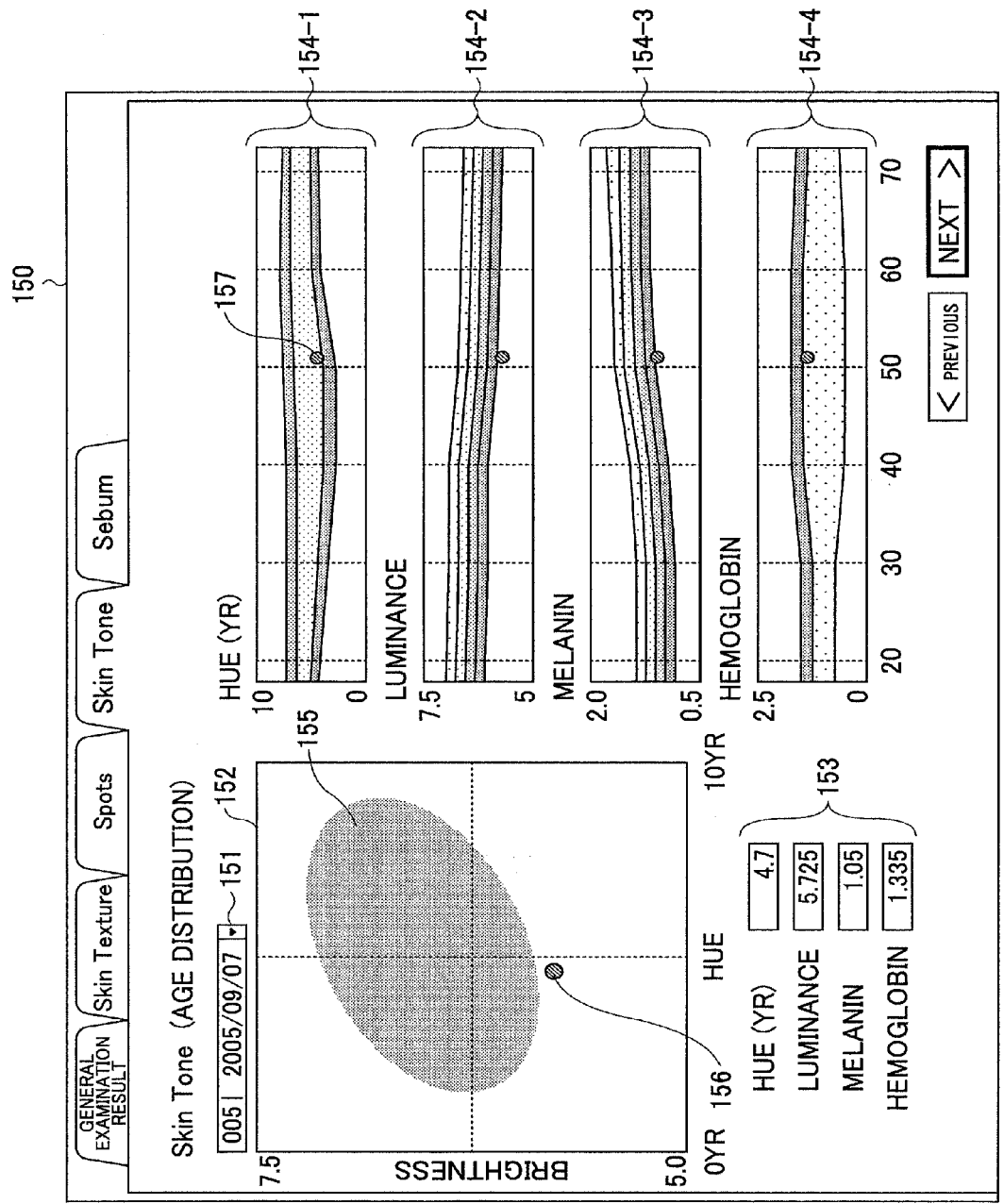
FIG. 21 is a diagram showing an exemplary skin tone display screen.

FIG. 21 is a diagram showing an exemplary skin tone display screen. The skin tone display screen 150 of FIG. 21 includes an examination date selection part 151, a brightness/hue correlation display area 152, an analysis display area 153, and age distribution display areas 154-1 through 154-4. The examination date selection part 151 may be a combo box, for example, that may be used to selectively display the skin tone analysis of a desired examination date by selecting the desired date from the log information including examination dates of examinations performed up to the present.

When the examination date is selected at the examination date selection part 151, a corresponding brightness/hue correlation is displayed at the brightness/hue correlation display area 152. It is noted that the brightness/hue correlation display area 152 displays a desirable correlation area 155 in a different color or with hatchings to distinguish this area as representing a desirable correlation between the brightness and hue. In this way, the positioning of the analysis result 156 for the examinee may be easily and accurately determined, for example. Also, evaluation results on the hue, brightness, melanin, and hemoglobin may be displayed at the analysis display area 153.

Further, the skin tone display screen 150 displays evaluation results 157 on the hue, brightness, melanin, and hemoglobin obtained for the examinee in relation to the age of the examinee in the age distribution display areas 154-1 through 154-4. It is noted that the horizontal axes of the age distribution display areas 154-1 through 154-4 represent the age, and the vertical axes represent corresponding evaluation values. As is described above, zones for classifying the evaluation results are displayed in the age distribution display areas 154-1 through 154-4. Therefore, the skin state analysis results of the examinee may be compared with data on the general skin states of persons in the same age group as the examinee to thereby enable accurate skin state analysis according to the examinee.

Figure 22:
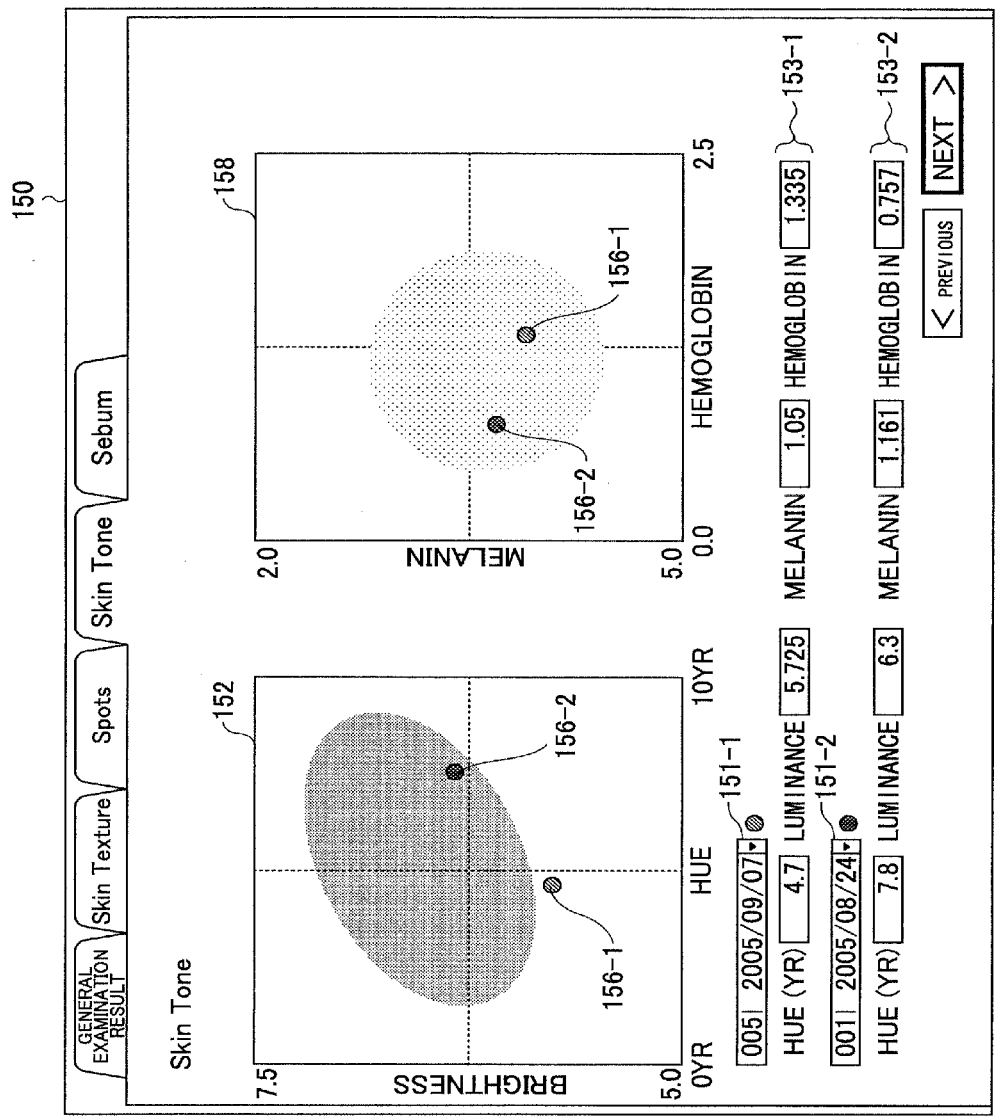
FIG. 22 is a diagram showing another exemplary skin tone display screen.

FIG. 22 is a diagram showing another exemplary skin tone display screen. In the display screen of FIG. 22, more than one examination date selection parts 151 and analysis display areas 153 may be provided to display plural evaluation results 156-1 and 156-2 obtained on plural examination dates based on the log information on the brightness/hue correlation display area 152. Further, a melanin/hemoglobin correlation display area 158 may be provided, and corresponding evaluation results 156-1 and 156-2 may be displayed on this melanin/hemoglobin correlation display area 158. It is noted that the plural evaluation results may be distinguished by being displayed in different colors or hatching patterns, for example. In this way, the progressive evaluation of the skin tone may be possible.

<Sebum Display Screen>

Figure 23:
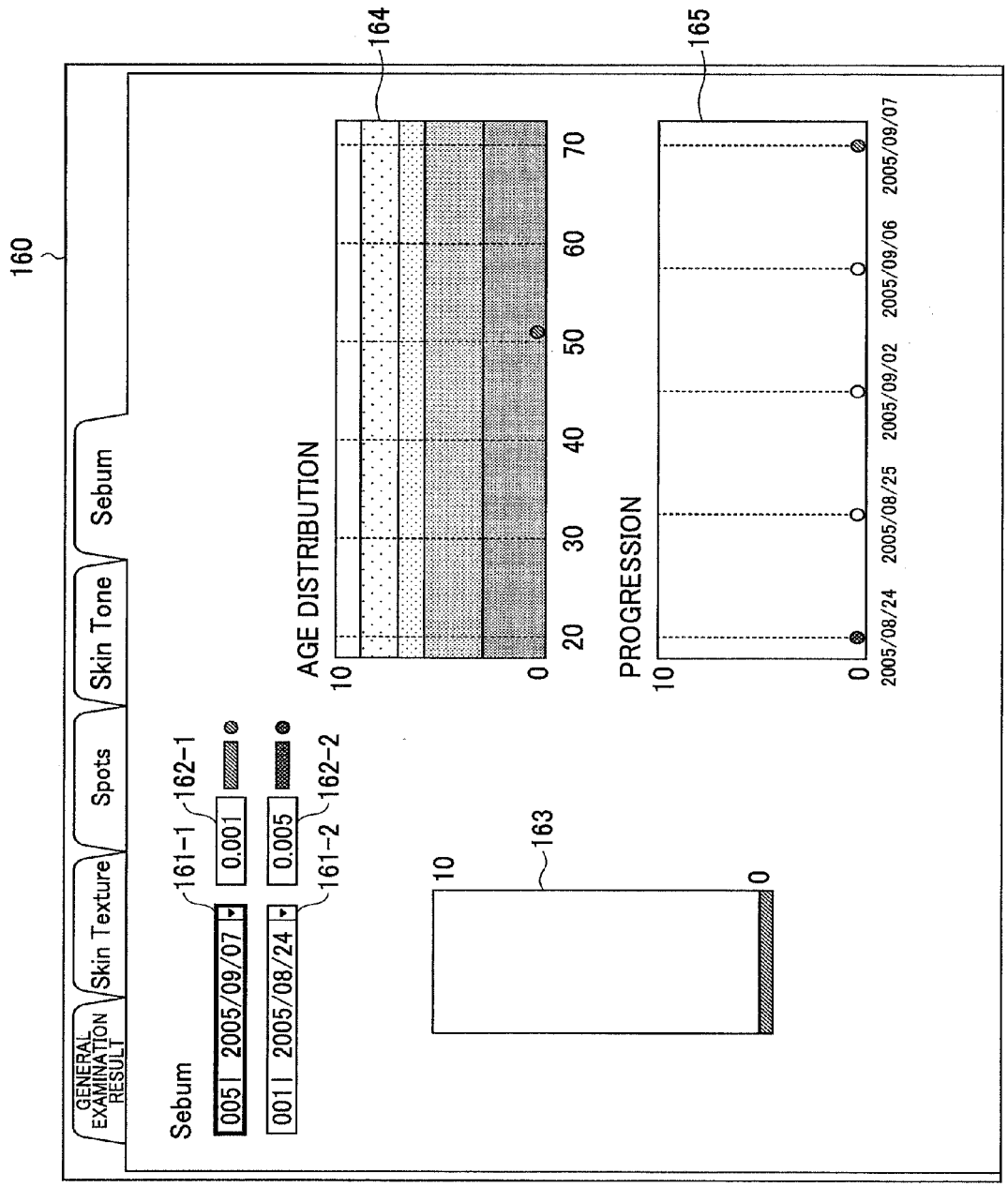
FIG. 23 is a diagram showing an exemplary sebum display screen.

FIG. 23 is a diagram showing an exemplary sebum display screen. The sebum display screen 160 shown in FIG. 23 includes at least one examination date selection part 161 for selecting at least one examination date, a sebum amount display part 162, a sebum amount display area 163, an age distribution display area 164, and an examination progression display area 165. In the sebum display screen 160 of the present example, both the age distribution display area 164 and the examination progression display area 165 may be displayed at the same time. Also, the sebum amount display area 163 graphically indicates the amount of sebum.

As is shown in FIG. 23, by displaying progressive information related to the amount of sebum, accurate skin analysis may be enabled.

It is noted that the above described display screens are merely illustrative examples, and other exemplary screens may be generated by combining different items of different screens to display progressive information for enabling accurate skin analysis, for example.

<Skin Texture/Pores Analysis Execution Screen>

Figure 24:
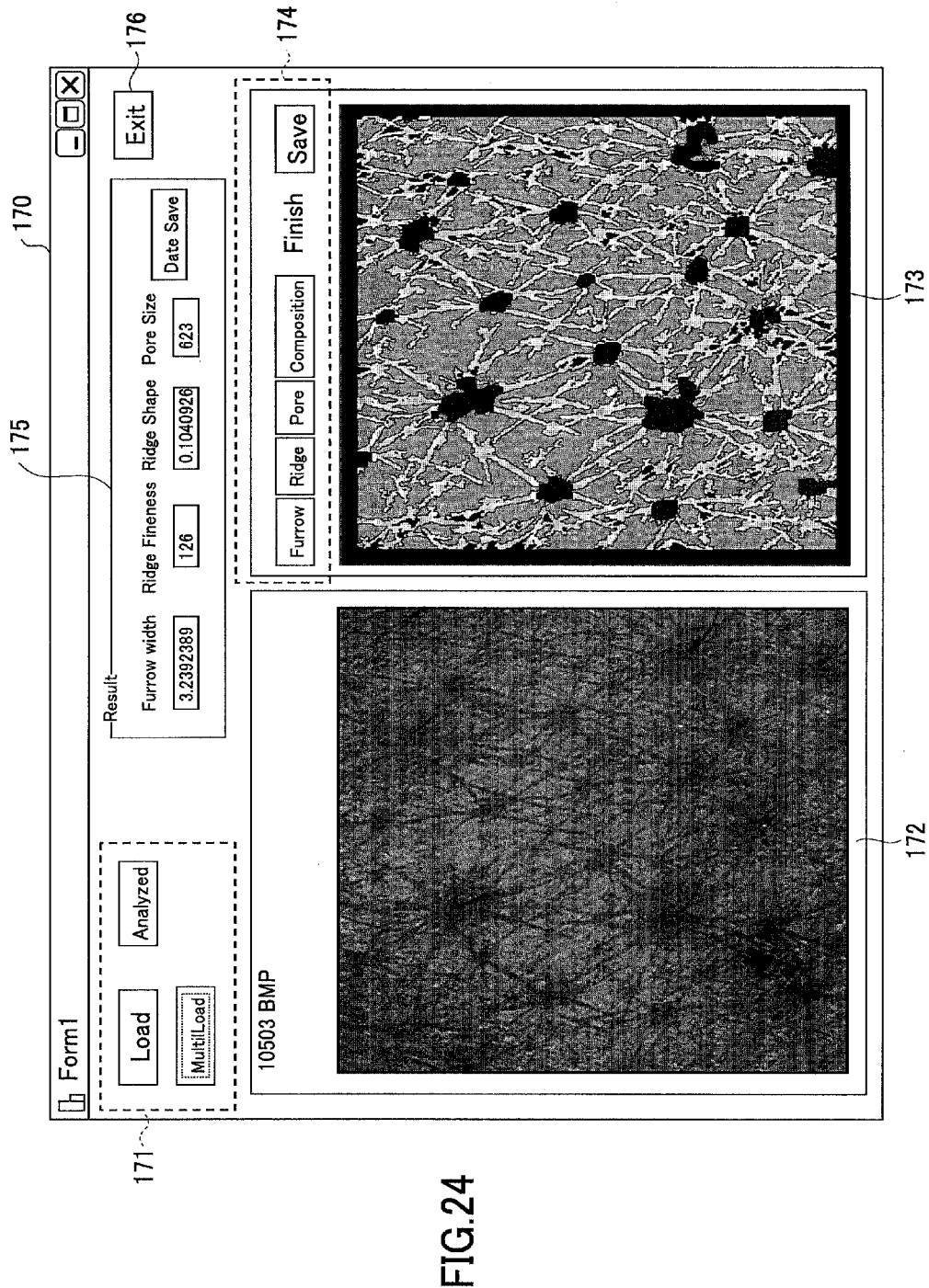
FIG. 24 is a diagram showing an exemplary skin texture/pores analysis execution screen according to an embodiment of the present invention.

According to an embodiment of the present invention, screens showing process step execution results of the above-described skin texture/pores analyzing process may be generated and displayed. FIG. 24 is a diagram showing an exemplary skin texture/pores analysis execution screen.

The skin texture/pores analysis execution screen 170 shown in FIG. 24 includes a main operation button area 171, an original image display area 172, an analysis image display area 173, an analysis image setting area 174, and an analysis result display area 175.

The main operation button area 171 is used to execute operations such as inputting (loading) an original image or analyzing the skin state, for example. It is noted that execution of a skin state analyzing process involves parameterizing at least one of the above-described parameters corresponding to the "pore size", "furrow width", "ridge fineness", and "ridge shape". Specifically, the process execution may involve generating only the pore size parameter, or generating all of the above parameters, for example.

Also, in executing image input operations, a predetermined storage area such as a folder or a drive unit may be selected so that plural images included in the selected storage area may be input (multiload) and skin state analyzing processes may be successively executed with respect to the plural images included in the selected storage area.

The original image display area 172 displays an original image subject to processing, and the analysis image display area 173 displays an image resulting from the skin state analyzing process. It is noted that the analysis image resulting from the analyzing process may be an image in which pore portions, furrow portions, and ridge portions are emphasized, for example. Specifically, differing pore portions, furrow portions, and ridge portions may be displayed in plural different colors so that the individual portions may be visually distinguished from one another. In particular, portions adjacent to each other may be displayed in different colors to clearly distinguish one from the other.

In this way, a user or some other observer may be able to easily determine the shapes, sizes, and numbers of pores, furrows and ridges. For example, even when adjacent pores, furrows, or ridges are only separated from one another by one pixel, determinations may be easily made as to whether these portions correspond to separate portions. Also, in addition to using different colors, certain locations may be indicated using hatchings or gratings to enable easy determination of what such locations are representing. Further, the color or hatching display pattern may be changed depending on the parameter value so that analysis results may be displayed in relation to conditions represented by the different colors. For example, when it is determined that a certain portion has a predetermined area, such a portion may be displayed in red.

The analysis image setting area 174 enables display of images representing the portions of furrows, ridges, pores, and compositions thereof. It is noted that images extracted in the processes illustrated in FIGS. 9, 11, and 13 may be used as the display images. Also, it is noted that the images displayed in this case may be emphasized images. The analysis image setting area 174 may only save the resulting analysis image of the skin state analyzing process.

The analysis result display area 175 displays the analysis results (parameters) of the furrow width, ridge fineness, ridge shape, and pore size. It is noted that in the example of FIG. 24, the parameters are represented by numerical values. However, the present invention is not limited to such an example, and in other examples, plural classes such as "good", "normal", "bad" may be defined in relation to numerical values and corresponding characters describing the classes may be displayed to represent the parameters. Also, the analysis result display area 175 may additionally display a determination of the skin age such as "skin of ages 20-23" or "skin of thirties", for example that are defined before hand based on the parameters. Also, the analysis result display area 175 enables saving (data save) of the displayed analysis results (parameter data).

By selecting an "exit" button 176 of the skin texture/pores analysis execution screen 170 shown in FIG. 24, the display screen may be closed and the corresponding analyzing process may be ended. It is noted that the sizes and layout of the display areas of the skin texture/pores analysis execution screen 170 is not limited to that shown in FIG. 24. For example, one or more of the display areas may be arranged to be displayed on a separate screen (window).

By executing the above-described processes via the skin texture/pores analysis execution screen shown in FIG. 24, accurate analysis of the skin texture/pores of the examinee may be enabled, for example. Also, images or other information obtained by executing processes via the above-described skin texture/pores analysis execution screen 170 may be displayed as the skin texture/pores analysis results shown in FIGS. 17-19, for example.

As can be appreciated from the above descriptions, according to embodiments of the present invention, multidimensional skin state analysis may be accurately performed.

Industrial Applicability

A skin state analyzing method, a skin state analyzing apparatus, and a medium storing a skin state analyzing program according to embodiments of the present invention may be used in the field of medicine or cosmetic product distribution, for example, to enable even non-experts to perform consistent and accurate skin diagnosis or beauty counseling based on analysis results represented by numerical values or progressive information displayed according to embodiments of the present invention. Also, skin state analyzing techniques according to embodiments of the present invention may be used in apparatuses that enable self-evaluation by user, for example.

The present application is based on and claims the benefit of the earlier filing date of Japanese Patent Application No. 2005-133275 filed on Apr. 28, 2005, and Japanese Patent Application No. 2005-32411 filed on Nov. 8, 2005, the entire contents of which are hereby incorporated by reference.

The invention claimed is:

1. A method for analyzing skin texture or pores of an examinee using an image of the skin of the examinee and a central processing unit (CPU), the method comprising:
    extracting, by using the CPU, R components, G components, and B components from the image with the CPU;
    extracting, by using the CPU, a pore image from the R components and one of the B components or G components by generating a difference image from the R components and one of the B components or one of the G components, and by subsequently removing furrows from the generated difference image to extract the pore image;
    generating, by using the CPU, a pore parameter pertaining to pore size from the pore image with the CPU;
    extracting, by using the CPU, a furrow image from the G components with the CPU;
    generating, by using the CPU, a furrow parameter pertaining to furrow width from the furrow image;
    extracting, by using the CPU, a ridge image from the pore image and the furrow image; generating a ridge parameter pertaining to ridge fineness and/or ridge shape from the ridge image; and
    analyzing, by using the CPU, the skin texture or pores using at least one of the pore parameter, the furrow parameter, and the ridge parameter.

2. The method as claimed in claim 1, wherein the pore parameter is generated by calculating, by using the CPU, an average area and/or a total area of pores of the pore image and generating, by using the CPU, the pore parameter based on the calculated area.

3. The method as claimed in claim 1, wherein the furrow image is extracted by performing, by using the CPU, a filtering process on an image of the G components using a differential filter for emphasizing the furrow shape to extract the furrow image.

4. The method as claimed in claim 1, wherein the furrow parameter is based on a furrow width obtained from the furrow image.

5. The method as claimed in claim 1, wherein the ridge image is extracted, using the CPU, by obtaining ridge portions from the furrow image, scaling down peripheries of the ridge portions by a predetermined number of pixels to generate a ridge separated image, and removing pores from the ridge separated image based on the pore image to extract the ridge image.

6. The method as claimed in claim 1, wherein the ridge parameter is based on an average area or a number of ridges within a predetermined image region of the ridge image, an average area or a number of ridges with respect to a face surface area of the examinee, and/or a ridge roundness.

7. The method as claimed in claim 1, further comprising:
    displaying at least one of the pore parameter, the furrow parameter, the ridge parameter, the pore image, the furrow image, and the ridge image in a distinguishing color, and displaying adjacent pores, furrows, and ridges using different colors.

8. A skin state analyzing apparatus for analyzing skin texture or pores of an examinee using an image of the skin of the examinee, the apparatus comprising:
    an optical system comprising:
        a camera for taking the image of the skin;
        a light source; and
        a deflection filter; and
    a mainframe computer coupled to the optical system, the mainframe computer comprising:
        a central processing unit (CPU);
        a storage device coupled to the CPU, the storage device comprising at least one of a hard drive, and a CD/ROM;
        an input device coupled to the CPU, the input device comprising at least one of a keyboard and a pointing device;
        an output device coupled to the CPU, the output means comprising at least one of a monitor, a speaker, and a printer; and
        an image input;
            wherein the CPU is configured to extract R components, G components, and B components from the image of the skin which is inputted through the image input from the camera, and configured to perform distortion correction of each of the extracted R, G, and B components by using a Gaussian filter;
            wherein the CPU is configured to extract a pore image from the R components and one of the B components or G components by subtracting the R components from either the B components or G components form the pore image from at least one of a R-B differential image, a B-R differential image, a R-G differential image, and a G-R differential image;
            wherein the CPU is configured to generate a pore parameter pertaining to pore size from the pore image;

wherein the CPU is configured to extract a furrow image from the G components;
wherein the CPU is configured to generate a furrow parameter pertaining to furrow width from the furrow image;
wherein the CPU is configured to extract a ridge image from the pore image and the furrow image;
wherein the CPU is configured to generate a ridge parameter pertaining to ridge fineness and/or ridge shape from the ridge image; and
wherein the CPU is configured to analyze skin texture or pores using at least one of the pore parameter, the furrow parameter, and the ridge parameter.

9. The skin state analyzing apparatus as claimed in claim 8, wherein the pore parameter is calculated using an average area and/or a total area of pores of the pore image and the pore parameter is based on the calculated area.

10. The skin state analyzing apparatus as claimed in claim 8, wherein the furrow image is extracted using a filtering process on an image of the G components using a differential filter for emphasizing the furrow shape to extract the furrow image.

11. The skin state analyzing apparatus as claimed in claim 8, wherein the furrow parameter is based on a furrow width obtained from the furrow image.

12. The skin state analyzing apparatus as claimed in claim 8, wherein the ridge image is extracted by obtaining ridge portions from the furrow image, scaling down peripheries of the ridge portions by a predetermined number of pixels to generate a ridge separated image, and removing pores from the ridge separated image based on the pore image to extract the ridge image.

13. The skin state analyzing apparatus as claimed in claim 8, wherein the ridge parameter is based on an average area or a number of ridges within a predetermined image region of the ridge image, an average area or a number of ridges with respect to a face surface area of the examinee, and/or a ridge roundness.

14. The skin state analyzing apparatus as claimed in claim 8, further comprising displaying at least one of the pore parameter, the furrow parameter, the ridge parameter, the pore image, the furrow image, and the ridge image in a distinguishing color, and displays adjacent pores, furrows, and ridges using different colors.

15. A non-transient computer-readable medium, that, when executed by a computer, causes the computer to:
extract R components, G components, and B components from the image;
extract a pore image from the R components and one of the B components or G components by generating a difference image from the R components and one of the B components or G components and by removing furrows from the generated difference image to extract the pore image;
generate a parameter pertaining to pore size from the pore image;
extract a furrow image from the G components;
generate a parameter pertaining to furrow width from the furrow image;
extract a ridge image from the pore image and the furrow image;
generate a parameter pertaining to ridge fineness and/or ridge shape from the ridge image; and analyze the skin texture or pores using at least one of the pore parameter, the furrow parameter, and the ridge parameter.

16. The non-transient computer-readable medium as claimed in claim 15, wherein the pore parameter is calculated using an average area and/or a total area of pores of the pore image and generates the pore parameter based on the calculated area.

17. The non-transient computer-readable medium as claimed in claim 15, wherein the furrow image is performed by a filtering process on an image of the G components using a differential filter for emphasizing the furrow shape to extract the furrow image.

18. The non-transient computer-readable medium as claimed in claim 15, wherein the furrow parameter is generated by the furrow parameter based on a furrow width obtained from the furrow image.

19. The non-transient computer-readable medium as claimed in claim 15, wherein the ridge image is obtained by using ridge portions from the furrow image, by scaling down peripheries of the ridge portions by a predetermined number of pixels to generate a ridge separated image, and by removing pores from the ridge separated image based on the pore image to extract the ridge image.

20. The non-transient computer-readable medium as claimed in claim 15, wherein the ridge parameter is generated based on an average area or a number of ridges within a predetermined image region of the ridge image, an average area or a number of ridges with respect to a face surface area of the examinee, and/or a ridge roundness.

21. The non-transient computer-readable medium as claimed in claim 15, further comprising displaying at least one of the pore parameter, the furrow parameter, the ridge parameter, the pore image, the furrow image, and the ridge image in a distinguishing color, and displays adjacent pores, furrows, and ridges using different colors.

* * * * *